United States Patent [19]

Doria et al.

[11] 4,341,780

[45] Jul. 27, 1982

[54] SUBSTITUTED PYRIDO [1,2-A] PYRIMIDINES USEFUL AS ANTI-ALLERGIC, ANTI-ULCER AND ANTI-DIABETIC AGENTS

[75] Inventors: Gianfederico Doria, Milan; Ciriaco Romeo, Serino; Piero Sberze, Varese; Marcellino Tibolla, Canale d'Agordo; Maria L. Corno, Milan, all of Italy

[73] Assignee: Farmitalia Carlo Erba S.p.A., Milan, Italy

[21] Appl. No.: 267,450

[22] Filed: May 27, 1981

Related U.S. Application Data

[63] Continuation of Ser. No. 138,879, Apr. 10, 1980, Pat. No. 4,310,526.

[30] Foreign Application Priority Data

May 8, 1979 [GB] United Kingdom ................. 7915810

[51] Int. Cl.³ ................... A61K 31/505; C07D 471/04
[52] U.S. Cl. ................... 424/248.55; 542/442; 542/443; 542/444; 544/282; 424/251

[58] Field of Search ............. 424/251, 248.55; 544/282; 542/442, 443, 444

[56] References Cited

U.S. PATENT DOCUMENTS 3,935,197  1/1976  Yale .................................. 544/282
4,209,622  6/1980  Meszaros et al. ................. 544/282

FOREIGN PATENT DOCUMENTS 869832  12/1978  Belgium .
873192  4/1979  Belgium .
873195  4/1979  Belgium .

OTHER PUBLICATIONS

Fieser, et al., "Reagents for Organic Synthesis," John Wiley & Sons, Inc., New York (1967), pp. 310–319.

*Primary Examiner*—Donald G. Daus
*Assistant Examiner*—Diana G. Rivers
*Attorney, Agent, or Firm*—Murray & Whisenhunt

[57] ABSTRACT

Substituted pyrido [1,2-a] pyrimidines and pharmaceutical compositions containing them, suitable for use as anti-allergy, anti-ulcer, and anti-diabetic agents.

29 Claims, No Drawings

SUBSTITUTED PYRIDO [1,2-a] PYRIMIDINES USEFUL AS ANTI-ALLERGIC, ANTI-ULCER AND ANTI-DIABETIC AGENTS

This is a continuation application of Ser. No. 138,879, filed Apr. 10, 1980, now U.S. Pat. No. 4,310,526.

The present invention relates to substituted pyrido[1,2-a]pyrimidines, to a process for their preparation and to pharmaceutical compositions containing them.

The invention provides compounds having the following general formula (1)

wherein A completes a bond, thereby providing a double bond between the 6- and 7-carbon atoms, or A represents a —$CH_2$- group, thereby providing a cyclopropane ring fused to the pyrido ring at the 6,7-position; $R_1$ represents a hydrogen atom or a $C_1$–$C_{12}$ alkyl group which is unsubstituted or substituted by a group, wherein each of $R_4$ and $R_5$ independently represents a hydrogen atom or a $C_1$–$C_{10}$ alkyl group, or $R_4$ and $R_5$, taken together with the nitrogen atom to which they are attached, form a N-pyrrolidinyl, piperidino or morpholino group; $R_2$ represents a hydrogen atom or a $C_1$–$C_6$ alkyl group or a $C_3$- or $C_4$-alkenyl group; $R_3$ represents (a) a furyl, thienyl or pyridyl group each of which is unsubstituted or substituted by a methyl group; or (b) a group of formula wherein each of $R_6$, $R_7$ and $R_8$ independently represents a hydrogen or halogen atom, a hydroxy group, a $C_1$–$C_4$ dialkylamino group, a group —$CF_3$ or a group —$R_9$ or —$OR_9$, where $R_9$ represents a $C_1$–$C_6$ alkyl or $C_3$- or $C_4$-alkenyl group and pharmaceutically acceptable salts thereof.

The compounds of the invention include also the pharmaceutically acceptable salts of the compounds of formula (I) as well as all possible isomers (e.g. cis or trans isomers) and the mixtures thereof. Preferably the group —CH=CH—$R_3$ is in the trans configuration.

The compounds in which A represents a —$CH_2$— group are herein designated 6,7-methylene compounds, in order to adopt a uniform system of nomenclature based on the pyridopyrimidine fused ring system. They can alternatively be regarded as 1,5-diaza-4-oxo-tricyclo[5.4.0.0] undeca-2,9,11-triene derivatives.

The numbering used to identify the position of the substituents in the $R_3$ radical is the conventional one, as is shown by the following examples:

(a) when $R_3$ is phenyl:

(b) when $R_3$ is pyridyl:

(c) when $R_3$ is furyl or thienyl:

wherein X is oxygen or sulphur.

The expression "in particular" wherever used herein is to be interpreted as particularising the subject matter prefaced thereby as a preference or further preference. It is not to be understood as limiting the preceding subject matter to the matter particularised.

The alkyl, alkenyl, alkoxy and alkenyloxy groups may be branched or straight chain groups.

When $R_1$ is an unsubstituted $C_1$–$C_{12}$ alkyl, it is preferably $C_1$–$C_6$ alkyl, preferably methyl, ethyl, isopropyl, t.-butyl or hexyl.

When $R_4$ and/or $R_5$ are $C_1$–$C_{10}$ alkyl, the alkyl group is preferably $C_1$–$C_4$ alkyl, preferably methyl, ethyl, isopropyl or t.-butyl.

$R_2$ is preferably $C_1$–$C_4$ alkyl, preferably methyl, n-propyl or n-butyl.

When $R_3$ is furyl, thienyl or pyridyl, it is preferably 2-furyl, 2-thienyl or 2-pyridyl.

When $R_9$ is $C_1$–$C_6$ alkyl, it is preferably methyl, ethyl, propyl or isopropyl. When $R_9$ is $C_3$–$C_4$ alkenyl, it is preferably propenyl.

Preferably $R_6$, $R_7$ and $R_8$ are independently selected from hydrogen, allyloxy, $C_1$–$C_4$ alkoxy, preferably methoxy, ethoxy, n-propoxy, isopropoxy or $C_1$–$C_4$ alkyl, preferably methyl or ethyl.

Examples of pharmaceutically acceptable salts are those with inorganic bases, e.g. sodium, potassium, calcium and aluminium salts or with organic bases, e.g. lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, methanesulphonic and ethanesulphonic acids. Preferred salts are the sodium and the potassium salts, as well as the hydrochlorides of the basic esters, e.g. the diethylaminoethyl and dimethylaminoethyl esters.

Particularly preferred compounds of the invention are those of formula (I) wherein R₁ is (a″) hydrogen (b″) C₁–C₆ alkyl unsubstituted or substituted by a

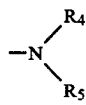

group, wherein each of R₄ and R₅, which are the same or different, is C₁–C₄ alkyl; (c″) 2-(N-pyrrolidinyl)-ethyl; R₂ is C₁–C₄ alkyl; R₃ is (a‴) phenyl unsubstituted or substituted by chlorine or C₁–C₄ alkyl, in particular methyl or ethyl, or C₁–C₄ alkoxy, in particular methoxy, ethoxy or isopropoxy; or (b‴) 2-furyl; 2-thienyl, 2-pyridyl, the furyl, the thienyl and the pyridyl groups being unsubstituted or substituted by a methyl group, as well as their pharmaceutically acceptable salts.

In the preferred compounds of the invention the COOR₁ group is a carboxylic acid group and the compounds are free acids or carboxylic acid salts.

Examples of particularly preferred compounds of the invention are:

2-trans-(2-phenyl-ethenyl)-3-propyl-4-oxo-4H-pyrido[1,2-a]pyrimidine-7-carboxylic acid;
2-trans-[2-(2-methyl-phenyl)-ethenyl]-3-propyl-4-oxo-4H-pyrido-[1,2-a]pyrimidine-7-carboxylic acid;
2-trans-[2-(3-chloro-phenyl)-ethenyl]-3-methyl-4-oxo-4H-pyrido-[1,2-a]pyrimidine-7-carboxylic acid;
2-trans-[2-(4-methyl-phenyl)-ethenyl]-3-propyl-4-oxo-4H-pyrido-[1,2-a]pyrimidine-7-carboxylic acid;
2-trans-[2-(3-methoxy-phenyl)-ethenyl]-3-propyl-4-oxo-4H-pyrido[1,2-a]pyrimidine-7-carboxylic acid;
2-trans-[2-(2-ethoxy-phenyl)-ethenyl]-3-propyl-4-oxo-4H-pyrido-[1,2-a]pyrimidine-7-carboxylic acid;
2-trans-[2-(2,3-dimethoxy-phenyl)-ethenyl]-3-propyl-4-oxo-4H-pyrido[1,2-a]pyrimidine-7-carboxylic acid;
2-trans-[2-(2-thienyl)-ethenyl]-3-methyl-4-oxo-4H-pyrido[1,2-a]pyrimidine-7-carboxylic acid;
2-trans-[2-(2-furyl)-ethenyl]-3-methyl-4-oxo-4H-pyrido[1,2-a]pyrimidine-7-carboxylic acid;
2-trans-(2-phenyl-ethenyl)-3-methyl-4-oxo-4H-pyrido[1,2-a]pyrimidine-7-carboxylic acid;
2-trans-[2-(2-methoxy-3-ethoxy-phenyl)-ethenyl]-3-ethyl-4-oxo-4H-pyrido[1,2-a]pyrimidine-7-carboxylic acid;
2-trans-[2-(2-methoxy-phenyl)-ethenyl]-3-ethyl-4-oxo-4H-pyrido[1,2-a]pyrimidine-7-carboxylic acid;
2-trans-[2-(3-methoxy-phenyl)-ethenyl]-3-ethyl-4-oxo-4H-pyrido[1,2-a]pyrimidine-7-carboxylic acid;
2-trans-[2-(4-methyl-phenyl)-ethenyl]-3-ethyl-4-oxo-4H-pyrido[1,2-a]pyrimidine-7-carboxylic acid;
2-trans-[2-(2,3-dimethoxy-phenyl)-ethenyl]-3-ethyl-4-oxo-4H-pyrido[1,2-a]pyrimidine-7-carboxylic acid;
2-trans-[2-(3-chloro-phenyl)-ethenyl]-4-oxo-4H-pyrido[1,2-a]pyrimidine-7-carboxylic acid;
2-trans-[2-(2-methoxy-3-ethoxy-phenyl)-ethenyl]-3-propyl-4-oxo-4H-pyrido[1,2-a]pyrimidine-7-carboxylic acid;
2-trans-(2-phenyl-ethenyl)-3-propyl-6,7-methylen-4-oxo-4H-pyrido[1,2-a]pyrimidine-7-carboxylic acid;
2-trans-(2-phenyl-ethenyl)-3-ethyl-6,7-methylen-4-oxo-4H-pyrido[1,2-a]pyrimidine-7-carboxylic acid;
2-trans-[2-(2-methyl-phenyl)-ethenyl]-3-ethyl-6,7-methylen-4-oxo-4H-pyrido[1,2-a]pyrimidine-7-carboxylic acid;
2-trans-[2-(3-methyl-phenyl)-ethenyl]-3-ethyl-6,7-methylen-4-oxo-4H-pyrido[1,2-a]pyrimidine-7-carboxylic acid;
2-trans-[2-(4-methyl-phenyl)-ethenyl]-3-ethyl-6,7-methylen-4-oxo-4H-pyrido[1,2-a]pyrimidine-7-carboxylic acid;
2-trans-[2-(2-methoxy-phenyl)-ethenyl]-3-ethyl-6,7-methylen-4-oxo-4H-pyrido[1,2-a]pyrimidine-7-carboxylic acid;
2-trans-[2-(3-methoxy-phenyl)-ethenyl]-3-ethyl-6,7-methylen-4-oxo-4H-pyrido[1,2-a]pyrimidine-7-carboxylic acid;
2-trans-[2-(2,3-dimethoxy-phenyl)-ethenyl]-3-ethyl-6,7-methylen-4-oxo-4H-pyrido[1,2-a]pyrimidine-7-carboxylic acid;
2-trans-[2-(2-methyl-phenyl)-ethenyl]-3-propyl-6,7-methylen-4-oxo-4H-pyrido[1,2-a]pyrimidine-7-carboxylic acid;
2-trans-[2-(2,3-dimethoxy-phenyl)-ethenyl]-3-propyl-6,7-methylen-4-oxo-4H-pyrido[1,2-a]pyrimidine-7-carboxylic acid;
2-trans-[2-(2-methoxy-3-ethoxy-phenyl)-ethenyl]-3-propyl-6,7-methylen-4-oxo-4H-pyrido[1,2-a]pyrimidine-7-carboxylic acid;
2-trans-[2-(2-methoxy-3-ethoxy-phenyl)-ethenyl]-3-ethyl-6,7-methylen-4-oxo-4H-pyrido[1,2-a]pyrimidine-7-carboxylic acid;

as well as the pharmaceutically acceptable salts thereof, in particular the sodium salts, and the basic esters (e.g. those with 2-diethylamino-ethanol and 2-dimethylamino-ethanol) and the C₁–C₆ alkyl esters thereof, in particular the methyl, ethyl, isopropyl, t-butyl and hexyl esters.

The compounds of the invention can be prepared by a process comprising:

(a) reacting a compound of formula (II)

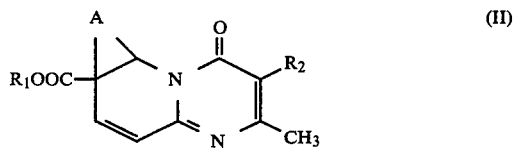

wherein

A, R₁ and R₂ are as defined above or a salt thereof, with an aldehyde of formula (III)

wherein R₃ is as defined above; or (b) cyclopropanating a compound of formula (IV)

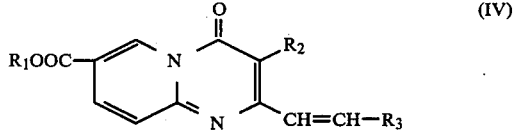

wherein

R₁, R₂ and R₃ are as defined above, or a salt thereof, so obtaining compounds of formula (I) wherein A is a group —CH₂—; or (c) hydrolyzing a compund of formula (V)

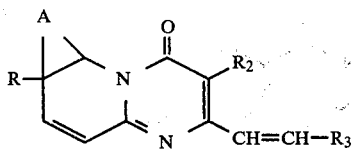

wherein
A, R$_2$ and R$_3$ are as defined above and R is cyano,

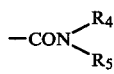

or a group

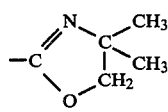

wherein R$_4$ and R$_5$ are as defined above, and, if desired, converting a compound of formula (I) into another compound of formula (I) and/or if desired, converting a compound of formula (I) into a pharmaceutically acceptable salt and/or, if desired, converting a salt into a free compound and/or, if desired, separating a mixture of isomers into the single isomers. The reaction of a compound of formula (II) with an aldehyde of formula (III) is preferably carried out in the presence of a basic condensing agent such as, for example, sodium ethoxide, sodium methoxide, sodium hydride, sodium amide, sodium hydroxide, in a solvent selected, e.g., from the group consisting of methanol, ethanol, isopropanol, dioxane, water and their mixtures, at a temperature preferably ranging between about 0° C. and 120° C. The cyclopropanation of a compound of formula (IV) may be carried out, for example, by reaction with dimethylsulphoxonium methylide (prepared e.g. according to the method described in J. Chem. Soc., 1967, 2495), operating in an inert organic solvent selected, e.g., from the group consisting of dimethylformamide, dimethylsulphoxide, dioxane and their mixtures; the temperature ranges preferably between about 0° C. and about 50° C. and the reaction time is generally less than 5 hours, preferably less than 2 hours. Preferably 1-3 moles, in particular 1-1.5 moles, of the reagent are used for one mole of the compound of formula (I).

The hydrolysis of compound of formula (V) may be carried out by conventional methods, for example by treatment with a base such as, e.g., NaOH, KOH, LiOH, or with an organic or inorganic acid such as, e.g., H$_2$SO$_4$, HCl, HBr, HI, H$_3$PO$_4$, in a solvent such as, for example, methanol, ethanol, dioxane, acetic acid, water and their mixtures, at a temperature ranging preferably from the room temperature and about 120° C. In particular, when R is the group

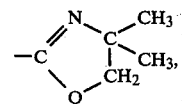

the hydrolysis is preferably carried out with an organic acid, such as formic, citric or oxalic acid in one of the above solvents or their mixtures.

A compound of formula (I) may be converted, as stated above, into another compound of formula (I) by known methods; for example, the compound of formula (I) wherein —COOR$_1$ is an esterified carboxy group, may be converted into a compound of formula (I) wherein —COOR$_1$ is carboxy by hydrolysis, e.g. basic hydrolysis, using, for example, sodium or potassium hydroxide, in a solvent, such as, e.g., water or a lower aliphatic alcohol, and operating at a temperature ranging from the room temperature to about 150° C., the same reaction may be also carried out e.g. by treatment with lithium bromide in dimethylformamide at a temperature higher than 50° C. A compound of formula (I) wherein —COOR$_1$ is carboxy may be converted into a compound of formula (I) wherein —COOR$_1$ is an esterified carboxy group, e.g. a carbalkoxy group unsubstituted or substituted by a

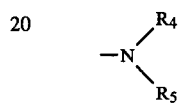

group, wherein R$_4$ and R$_5$ are as defined above, by conventional methods, for example by reacting the alkaline salt of the acid with the suitable alkyl halide, in an inert solvent, such as, e.g., acetone, dioxane, dimethylformamide, or hexamethylphosphortriamide at a temperature ranging from about 0° C. to about 100° C.

Alternatively the esterification of a compound of formula (I) may be effected by (a') converting the compound of formula (I) wherein —COOR$_1$ is carboxy into the corresponding halocarbonyl, preferably chlorocarbonyl, derivative, by reaction, e.g., with the desired acid halide, for example oxalyl chloride, thionyl chloride, PCl$_3$, PCl$_5$ or POCl$_3$, either in the absence of solvents or in an inert organic solvent such as, e.g., benzene, toluene, xylene, dioxane, dichloroethane, methylene chloride, or tetrahydrofurane, at a temperature ranging preferably from about 0° C. to about 120° C.; and then (b') reacting the obtained halocarbonyl derivative with the suitable alcohol of formula R$_1$—OH, wherein R$_1$ is as defined above, in an inert solvent such as, e.g., benzene, toluene, xylene, dioxane, dichloroethane, methylene chloride or tetrahydrofurane, at temperatures varying between about 0° C. and about 120° C., preferably in the presence of a base, such as, e.g., triethylamine or diethylamine. Free hydroxy groups, as substituents in R$_3$, may be, for example, etherified by reacting with an alkyl halide of formula R$_9$X, wherein R$_9$ is as defined above and X is chlorine, bromine or iodine, operating in the presence of a base such as for example NaOH, KOH, Na$_2$CO$_3$, K$_2$CO$_3$, NaH, NaNH$_2$, sodium methoxide, sodium ethoxide, in a solvent selected from the group consisting, for example, of methanol, ethanol, dioxane, acetone, dimethylformamide, hexamethylphosphortriamide, tetrahydrofurane, water and their mixtures at a temperature ranging preferably between about 0° C. and about 150° C. Furthermore the etherified hydroxy groups may be converted into free hydroxy groups, for example, by treatment with pyridine hydrochloride or with a strong acid such as, e.g., HCl, HBr, HI, or with a Lewis acid such as, e.g. AlCl$_3$, BBr$_3$.

Also the optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optionally active base and subsequent fractional crystallization. Thus, the separation of a mixture of geometric isomers may be carried out, for example, by fractional crystallization.

The compounds of formula (II) wherein A is a bond, may be, for example, prepared cyclizing a compound of formula (VI)

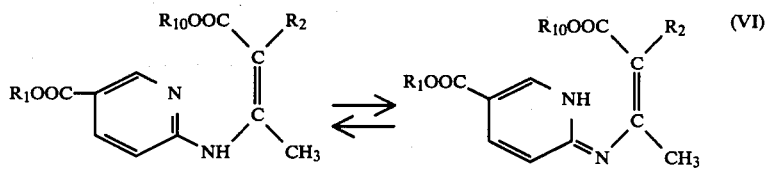

wherein $R_1$, $R_2$ are as defined above and $R_{10}$ is hydrogen or lower alkyl, preferably methyl or ethyl.

The cyclization of a compound of formula (VI) may be, for example, carried out in the presence of an acid catalyst, such as, for example, polyphosphoric acid*, HCl, HBr, HI, sulphuric acid, p-toluenesulphonic acid, at a temperature ranging preferably between 50° C. and 250° C.; the cyclization reaction may be carried out in an inert organic solvent selected, e.g., from the group consisting of a $C_1$–$C_6$ aliphatic alcohol, dimethylformamide, dioxane, tetrahydrofuran, benzene, toluene, xylene, acetic acid, ethylene glycol monomethyl ether and their mixtures, but it is preferably carried out in the absence of a solvent.

*Polyphosphoric acid means a mixture of equal weights of 99% $H_3PO_4$ and $P_2O_5$ The compounds of formula (II) wherein A is the group —$CH_2$—, may be prepared, for example, by cyclopropanating a compound of formula (II) wherein A is a bond, using the same experimental conditions defined above for the cyclopropanation of the compounds of formula (IV).

The compounds of formula (IV) may be prepared, for example, by reacting a compound of formula (II) wherein A is a bond with an aldehyde of formula (III), using the same experimental conditions as defined above.

The compounds of formula (V) may be prepared, for example, by reacting a compound of formula (VII)

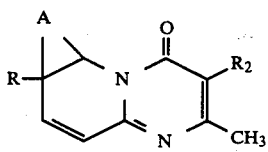

wherein A, R and $R_2$ are as defined above, with an aldehyde of formula (III) using the same experimental conditions defined above for the reaction of the latter with a compound of formula (II).

Alternatively the compounds of formula (V) wherein A is a group —$CH_2$— may be prepared by cyclopropanating a compound of formula (VIII)

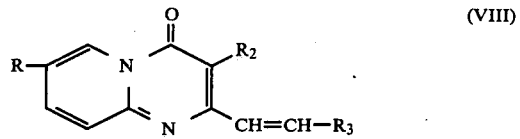

wherein R, $R_2$ and $R_3$ are as defined above, using the same experimental conditions defined above for the cyclopropanation of the compounds of formula (IV).

The compounds of formula (VI) may be prepared, for example, by reacting a compound of formula (IX)

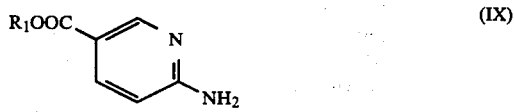

wherein $R_1$ is as defined above, with a compound of formula (X)

wherein $R_2$ and $R_{10}$ are as defined above; the reaction between a compound of formula (IX) and a compound of formula (X) may be, for example, carried out using the same experimental conditions defined above for the cyclization of the compounds of formula (VI). The compounds of formula (VII) wherein A is a bond may be prepared, for example, cyclizing a compound of formula (XI)

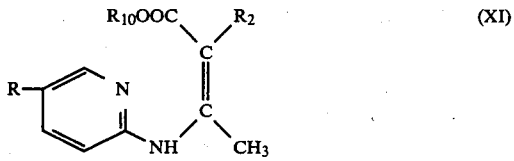

wherein R, $R_2$ and $R_{10}$ are as defined above, operating in the same experimental conditions defined above for the cyclization of the compound of formula (VI).

The compounds of formula (VII) wherein A is a group —$CH_2$— may be prepared, for example, by cyclopropanating a compound of formula (VII) wherein A is a bond, using the same experimental conditions defined above for the cyclopropanation of the compounds of formula (IV).

The compounds of formula (XI) may be prepared by reacting for example, a compound of formula (XII)

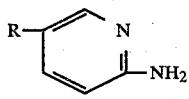

(XII)

wherein R is as defined above, with a compound of formula (X), using the same experimental conditions defined above for the synthesis of the compounds of formula (VI). The compounds of formula (III), (X) and (XII) are known compounds and may be prepared by conventional methods: in some cases they are commercially available products.

The compounds of the invention have anti-allergic activity, and are therefore useful in the prevention and treatment of all the affections of allergic origin, e.g. bronchial asthma, allergic rhinitis, hay fever, urticaria and dermatosis. The anti-allergic activity of the compounds of the invention is shown, e.g., by the first that they are active in the passive cutaneous anaphylaxis (PCA) test in rats, according to Goose J. and Blair A. M. J. N. (Immunology, 16, 749, 1969). An important peculiarity of the compounds of the invention is that they exhibit high levels of anti-allergic activity also when administered orally.

The following table shows the activity values obtained in the PCA test in rats, after oral administration, for a number of compounds of this invention, identified by the codes: K 13808, FCE 20509, K 13830, FCE 20099, FCE 20183, FCE 20461 and FCE 20188, in comparison with the well known anti-allergic drug Disodium Cromoglycate (DSCG).

The activity data are expressed in terms of $K_B$ defined as the dose of active compound capable of reducing to one half the activity of the serum used for the sensitization:

$$K_B = B/(DR-1)$$

wherein

B = dose of antagonist compound expressed in mg/kg;

DR = dose ratio: antilogarithm of the distance between the Log dose effect functions of the scrum with and without antagonist (J. H. Gaddum et al, Exp. Physiol., 1955, 40, 49).

The $K_B$ is adopted here because this value is independent both of the dose of the drug and the reagin concentration used for the sensitization.

The lower the $K_B$ value, the higher the anti-allergic activity.

In the following table the compounds of the invention are identified by the codes:

K 13808: 2-trans-(2-phenyl-ethenyl)-3-propyl-4-oxo-4H-pyrido[1,2-a]pyrimidine-7-carboxylic acid K 13830: 2-trans-(2-phenyl-ethenyl)-3-ethyl-6,7-methylen-4-oxo-4H-pyrido[1,2-a]pyrimidine-7-carboxylic acid FCE 20099: 2-trans-[2-(2-methyl-phenyl)-ethenyl]-3-propyl-4-oxo-4H-pyrido[1,2-a]pyrimidine-7-carboxylic acid FCE 21083: 2-trans-[2-(3-methoxy-phenyl)-ethenyl]-3-propyl-4-oxo-4H-pyrido[1,2-a]pyrimidine-7-carboxylic acid FCE 20188: 2-trans-(2-phenyl-ethenyl)-3-propyl-6,7-methylen-4-oxo-4H-pyrido[1,2-a]pyrimidine-7-carboxylic acid FCE 20509: 2-trans-[2-(3-methoxy-phenyl)-ethenyl]-3-ethyl-6,7-methylen-4-oxo-4H-pyrido[1,2-a]pyrimidine-7-carboxylic acid FCE 20461: 2-trans-[2-(2,3-dimethoxy-phenyl)-ethenyl]-3-propyl-6,7-methylen-4-oxo-4H-pyrido[1,2-a]pyrimidine-7-carboxylic acid.

| Compound | Pretreatment time | Anti-allergic activity $K_B$(mg/kg)- p.o. |
|---|---|---|
| FCE 20188 | 15' | 2.34 |
| K 13830 | 15' | 1.15 |
| FCE 20183 | 15' | 1.48 |
| FCE 20099 | 15' | 2.02 |
| K 13808 | 15' | 2.16 |
| FCE 20509 | 15' | 0.61 |
| FCE 20461 | 15' | 1.22 |
| Disodium Cromoglycate | 15' | >200 |

The anti-allergic activity was determined e.g. by the inhibition of the IgE-mediated PCA according to Goose J. and Blair A. M. J. N. (Immunology, 16, 749, 1969) using homocytotropic antibodies raised in rats following the method of Mota I., Immunology, 7, 681, (1964).

The tested compounds were administered per os (p.o) 15 minutes before the administration of the antigen: at least 6 rats were used for each dose.

The compounds of the present invention furthermore possess anti-ulcer activity, as demonstrated, e.g. by the fact that they proved to be active in inhibiting stress-induced ulcers in rats undergoing restraint in a water bath at 25° C. for 40 minutes according to a modification of the technique described by Takagi K. and Okabe S. (Jap. J. of Pharmacology., 1968, 19: 9).

In addition to the antiallergic activity, the compounds of this invention, in particular the compounds of formula (I) wherein $R_2$ is hydrogen or methyl, are useful as antidiabetic agents, as shown, for example, by the fact that they are effective in reducing the hyperglycemic effect of glucosamine in the mouse.

In view of their high therapeutic index the compounds of the invention can be safely used in medicine.

For example, the approximate acute toxicity (LD50) of the compound 2-trans-(2-phenyl-ethenyl)-3-propyl-4-oxo-4H-pyrido(1,2-a)pyrimidine-7-carboxylic acid in the mouse, determined with single adminstration of increasing doses and measured on the seventh day of treatment is per os higher than 800 mg/kg. Analogous toxicity data have been found for the other compounds of the invention.

The compounds of the invention may be administered in conventional manner, for instance, in the treatment of allergies, e.g. bronchial asthma, orally and parenterally, at a daily dosage preferably of 0.5 to 15 mg/kg, or by inhalation, preferably at a daily dosage of 0.5 to 100 mg. preferably 0.5 to 25 mg, or by topical application (for example for the treatment of urticaria and dermatosis), e.g., by a cream containing about 0.5–5 mg, preferably 1–2 mg, of active principle per 100 mg of cream. In the treatment of diabetes the compounds of the invention may be administered orally, at a daily dosage preferably of 500 to 1000 mg.

The nature of the pharmaceutical compositions containing the compounds of the invention in association with pharmaceutically acceptable carriers or diluents will, of course, depend upon the therapeutic use and the desired mode of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, drops, suppositories, or creams, or lotions for topical use.

Thus, for oral administration, the pharmaceutical compositions containing the compounds of this invention, are preferably tablets, pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as for example, starches, gelatine, methylcellulose, carboxymethylcellulose, gum-arabic, tragacanth, polyvinylpyrrolidone; disintegrating agents, such as for instance, starches, alginic acid, alginates, sodium starch glycolate; effervescing mixtures; dyestuffs; sweeteners; wetting agents, such as for instance, lecithin, polysorbates, lauryl sulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, e.g. an aerosol dispenser. When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g. lecithin.

The compounds of the invention may also be administered in the form of powders by means of a suitable insufflator device and in this case the fine particle sized powders of the active ingredient may be mixed with a diluent material such as lactose.

Furthermore, the compounds of this invention may also be administered by intradermal or intravenous injection in the conventional manner.

In addition to the internal administration, the compounds of this invention may find use in compositions for topical application, e.g. as creams, lotions or pastes for use in dermatological treatments. For these compositions the active ingredient may be mixed with conventional oleaginous or emulsifying excipients.

The following examples illustrate but do not limit the present invention.

EXAMPLE 1

Methyl 6-amino-nicotinate(4 g) was reacted with ethyl 2-propylacetoacetate(17.3 g) in the presence of p-toluensulphonic acid (0.16 g) under stirring at 150° C. for 42 hours. After cooling and dilution with hexane the precipitate was filtered and crystallized from methanol, thus giving 2.9 g of 2-methyl-3-propyl-4-oxo-4H-pyrido[1.2-a]pyrimidine-7-carboxylic acid methyl ester m.p. 98°–99° C., which were reacted with benzaldehyde (7 g) in methanol (100 ml), in the presence of sodium methoxide (1.78 g), under stirring at reflux temperature for 144 hours. After cooling the reaction mixture was concentrated in vacuo and diluted with ethyl ether: the precipitate was filtered, washed with ether and then dissolved in water. After acidification with acetic acid the precipitate was filtered and washed with water until neutral: crystallization with methanol gave 1.1 g of 2-trans-(2-phenyl-ethenyl)-3-propyl-4-oxo-4H-pyrido[1,2-a]pyrimidine-7-carboxylic acid, m.p. 250°–252° C., NMR (DMSO d6): vinylic protons $\delta_{H\beta}=7.60$(d), $\delta_{H\alpha}=8.05$(d) p.p.m., $J_{H\alpha H\beta}=16$ Hz.

By preceeding analogously, starting from suitable substituted benzaldehydes, the following compounds were prepared:

2-trans[2-(2-methyl-phenyl)-ethyenyl]-3-propyl-4-oxo-4H-pyrido[1,2-a]pyrimidine-7-carboxylic acid, m.p. 258°–259° C., NMR(CF₃COOD); vinylic protons $\delta_{H\beta}=7.36$(d), $\delta_{H\alpha}=8.18$(d) p.p.m., $J_{H\alpha H\beta}=16$ Hz.

2-trans[2-(3-methyl-phenyl)-ethenyl]-3-propyl-4-oxo-4H-pyrido[1,2-a]pyrimidine-7-carboxylic acid, m.p. 232°–235° C.;

2-trans-[2-(4-methyl-phenyl)-ethenyl]-3-propyl-4-oxo-4H-pyrido[1,2-a]pyrimidine-7-carboxylic acid; m.p. 245°–247° C.;

2-trans-[2-(2-methoxy-phenyl)-ethenyl]-3-propyl-4-oxo-4H-pyrido[1,2-a]pyrimidine-7-carboxylic acid, m.p. 274°–275° C., NMR(CF₃COOD); vinylic protons $\delta_{H\beta}=7.62$(d), $\delta_{H\alpha}=8.22$(d) p.p.m., $J_{H\alpha H\beta}=16$ Hz;

2-trans-[2-(3-methoxy-phenyl)-ethyl]-3-propyl-4-oxo-4H-pyrido[1,2-a]pyrimidine-7-carboxylic acid; m.p. 233°–236° C.;

2-trans-[2-(2,4-dimethyl-phenyl)-ethenyl]-3-propyl-4-oxo-4H-pyrido[1,2-a]pyrimidine-7-carboxylic acid, m.p. 311°–313° C.;

2-trans-[2-(2-ethoxy-phenyl)-ethenyl]-3-propyl-4-oxo-4H-pyrido[1,2-a]pyrimidine-7-carboxylic acid; m.p. 234°–235° C.;

2-trans-[2,-(2-isopropoxy-phenyl)-ethenyl]-3-propyl-4-oxo-4H-pyrido[1,2-a]pyrimidine-7-carboxylic acid; m.p. 225°–227° C.;

2-trans-[2-(2-allyloxy-phenyl)-ethenyl]-3-propyl-4-oxo-4H-pyrido[1,2-a]pyrimidine-7-carboxylic acid, m.p. 218°–219° C.;

2-trans-[2-(3,4-dimethoxy-phenyl)-ethenyl]-3-propyl-4-oxo-4H-pyrido[1,2-a]pyrimidine-7-carboxylic acid; m.p. 275°–280° C.;

2-trans-[2-(2,4-dimethoxy-phenyl)-ethenyl]-3-propyl-4-oxo-4H-pyrido[1,2-a]pyrimidine-7)carboxylic acid;

2-trans-[2-(2-propoxy-phenyl)-ethenyl]-3-propyl-4-oxo-4H-pyrido[1,2-a]pyrimidine-7-carboxylic acid;

2-trans-[2-(4-methoxy-phenyl)-ethenyl]-3-propyl-4-oxo-4H-pyrido[1,2-a]pyrimidine-7-carboxylic acid; m.p. 240°–242° C.;

2-trans-[2-(3-ethoxy-phenyl)-ethenyl]-3-propyl-4-oxo-4H-pyrido[1,2-a]pyrimidine-7-carboxylic acid; m.p. 222°–225° C.;

2-trans-[2-(3-isopropoxy-phenyl)-ethenyl]-3-propyl-4-oxo-4H-pyrido[1,2a]pyrimidine-7-carboxylic acid;

2-trans-[2-(2,5-dimethyl-phenyl)-ethenyl]-3-propyl-4-oxo-4H-pyrido[1,2-a]pyrimidine-7-carboxylic acid; m.p. 248°–249° C.;

2trans-[2-(2,3-dimethoxy-phenyl)-ethenyl]-3-propyl-4-oxo-4H-pyrido[1,2-a]pyrimidine-7-carboxylic acid; m.p. 205°-210° C.(dec.);

2-trans-[2-(3,5-dimethoxy-phenyl)-ethenyl]-3-propyl-4-oxo-4H-pyrido[1,2-a]pyrimidine-7-carboxylic acid; m.p. 279°-280° C.;

2-trans-[2-(2,5-dimethoxy-phenyl)-ethenyl]-3-propyl-4-oxo-4H-pyrido[1,2-a]pyrimidine-7-carboxylic acid; m.p. 268°-270° C., NMR(CF$_3$COOD): vinylic protons $\delta_{H\beta}$=7.55(d), $\delta_{H\alpha}$=8.11(d) p.p.m., $J_{H\alpha H\beta}$=16 Hz;

2-trans-[2-(2-methoxy-3-ethoxy-phenyl)-ethenyl]-3-propyl-4-oxo-4H-pyrido[1,2-a]pyrimidine-7-carboxylic acid; m.p. 220°-222° C.;

2-trans-[2-(2-ethoxy-3-methoxy-phenyl)-ethenyl]-3-propyl-4-oxo-4H-pyrido[1,2-a]pyrimidine-7-carboxylic acid; m.p. 209°-211° C.;

2-trans-[2-(2,3-diethoxy-phenyl)-ethenyl]-3-propyl-4-oxo-4H-pyrido[1,2-a]pyrimidine-7-carboxylic acid; m.p. 226°-228° C.;

2-trans-[2-(2-ethoxy-5-methoxy-phenyl)-ethenyl]-3-propyl-4-oxo-4H-pyrido[1,2-a]pyrimidine-7-carboxylic acid;

2-trans-[2-(2,3,4-trimethoxy-phenyl)-ethenyl]-3-propyl-4-oxo-4H-pyrido[1,2-a]pyrimidine-7-carboxylic acid;

2-trans-[2-(2,4,5-trimethoxy-phenyl)-ethenyl]-3-propyl-4-oxo-4H-pyrido[1,2-a]pyrimidine-7-carboxylic acid; m.p. 277°-279° C.;

2-trans-[2-(3,4,5-trimethoxy-phenyl)-ethenyl]-3-propyl-4-oxo-4H-pyrido[1,2-a]pyrimidine-7-carboxylic acid;

2-trans-[2-(2-chloro-phenyl)-ethenyl]-3-propyl-4-oxo-4H-pyrido[1,2-a]pyrimidine-7-carboxylic acid;

2-trans-[2-(4-chloro-phenyl)-ethenyl]-3-propyl-4oxo-4H-pyrido[1,2-a]pyrimidine-7-carboxylic acid;

2-trans-[2-(4-fluoro-phenyl)-ethenyl]-3-propyl-4-oxo-4H-pyrido[1,2-a]pyrimidine-7-carboxylic acid.

EXAMPLE 2

By proceeding according to example 1, starting from suitable 3-substituted methyl esters of 2-methyl-4-oxo-4H-pyrido[1,2-a]pyrimidine-7-carboxylic acid and benzaldheyde, the following compounds were prepared:

2-trans-(2-phenyl-ethenyl)-4-oxo-4H-pyrido[1,2-a]pyrimidine-7-carboxylic acid; m.p. 293°-295° C., NMR (DMSO d6): vinylic protons $\delta_{H\beta}$=7.18(d), $\delta_{H\alpha}$=8.00(d) p.p.m., $J_{H\alpha H\beta}$=16 Hz;

2-trans-(2-phenyl-ethenyl)-3-ethyl-4-oxo-4H-pyrido[1,2-a]pyrimidine-7-carboxylic acid; m.p. 265°-267° C., NMR (CF$_3$COOD—CDCl$_3$): vinylic protons $\delta_{H\beta}$=7.37(d), $\delta_{H\alpha}$=7.81(d) p.p.m., $J_{H\alpha H\beta}$=16 Hz;

2-trans-(23-phenyl-ethenyl)-3-methyl-4-oxo-4H-pyrido[1,2-a]pyrimidine-7-carboxylic acid; m.p. 312°-314° C., NMR (CF$_3$COOD): vinylic protons $\delta_{H\beta}$=7.44(d), $\delta_{H\alpha}$=7.85(d) p.p.m., $J_{H\alpha H\beta}$=16 Hz;

2-trans-(2-phenyl-ethenyl)-3-butyl-4-oxo-4H-pyrido[1,2-a]pyrimidine-7-carboxylic acid; m.p. 242°-243° C., NMR (CF$_3$COOD): vinylic protons $\delta_{H\beta}$=7.42(d), $\delta_{H\alpha}$=7.84(d) p.p.m., $J_{H\alpha H\beta}$=16 Hz;

2-trans-(2-phenyl-ethenyl)-3-trans-(propen-1-yl)-4-oxo-4H-pyrido[1,2-a]pyrimidine-7-carboxylic acid; m.p. 220° C.(dec.), NMR (CDCl$_3$/CF$_3$COOD) δ:2.09(b.d) (—CH=CH—CH$_3$), 6.53(d) (—CH=CH—CH$_3$), 6.66-7.03(m) —(CH=CH—CH$_3$), J=16 Hz, 7.4(d) (H$_\beta$ vinylic proton), 7.78(d) (H$_\alpha$ vinylic proton) $J_{H\alpha H\beta}$=16 Hz.

EXAMPLE 3

By proceeding according to Examples 1 and 2 the following compounds were prepared:

2-trans-[2-(2-thienyl)-ethenyl]-3-propyl-4-oxo-4H-pyrido[1,2-a]pyrimidine-7-carboxylic acid; m.p. 215°-217° C.;

2-trans-[2-(5-methyl-2-thienyl)-ethenyl]-3-propyl-4-oxo-4H-pyrido[1,2-a]pyrimidine-7-carboxylic acid;

2-trans-[2-(5-methyl-2-furyl)-ethenyl]-3-propyl-4-oxo-4H-pyrido[1,2-a]pyrimidine-7-carboxylic acid;

2-trans-[2-(2-pyridyl)-ethenyl]-3-propyl-4-oxo-4H-pyrido[1,2-a]pyrimidine-7-carboxylic acid; m.p. 280°-290° C.(dec.);

2-trans-[2-(6-methyl-2-pyridyl-ethenyl]-3-propyl-4-oxo-4H-pyrido[1,2-a]pyrimidine-7-carboxylic acid;

2-trans-[2-(3-pyridyl)-ethenyl]-3-propyl-4-oxo-4H-pyrido[1,2-a]pyrimidine-7-carboxylic acid;

2-trans-[2-(2-furyl)-ethenyl]-3-propyl-4-oxo-4H-pyrido[1,2-a]pyrimidine-7-carboxylic acid;

EXAMPLE 4

By proceeding according to Examples 1, 2 and 3, starting from ethyl 2-ethyl-acetoacetate and ethyl 2-butyl-acetoacetate, the following compounds were prepared:

2-trans-[2-(2-methyl-phenyl)-ethenyl]-3-ethyl-4-oxo-4H-pyrido[1,2-a]pyrimidine-7-carboxylic acid; m.p. 281°-282° C.;

2-trans-[2-(2-methyl-phenyl)-ethenyl]-3-butyl-4-oxo-4H-pyrido[1,2-a]pyrimidine-7-carboxylic acid; m.p. 231°-233° C.;

2-trans-[2-(3-methyl-phenyl)-ethenyl]-3-ethyl-4-oxo-4H-pyrido[1,2-a]pyrimidine-7-carboxylic acid; m.p. 280°-281° C.;

2-trans-[2-(3-methyl-phenyl)-ethenyl]-3-butyl-4-oxo-4H-pyrido[1,2-a]pyrimidine-7-carboxylic acid;

2-trans-[2-(4-methyl-phenyl)-ethenyl]-3-ethyl-4-oxo-4H-pyrido[1,2-a]pyrimidine-7-carboxylic acid; m.p. 291°-292° C.;

2-trans-[2-(4-methyl-phenyl)-ethenyl]-3-butyl-4-oxo-4H-pyrido[1,2-]pyrimidine-7-carboxylic acid;

2-trans-[2-(3-methoxy-phenyl)-ethenyl]-3-ethyl-4-oxo-4H-pyrido[1,2-a]pyrimidine-7-carboxylic acid; m.p. 259°-261° C.;

2-trans-[2-(3-methoxy-phenyl)-ethenyl]-3-butyl-4-oxo-4H-pyrido[1,2-a]pyrimidine-7-carboxylic acid; m.p. 212°-214° C.;

2-trans-[2-(3-ethoxy-phenyl)-ethenyl]-3-ethyl-4-oxo-4H-pyrido[1,2-a]pyrimidine-7-carboxylic acid; m.p. 247°-249° C.;

2-trans-[2-(3-ethoxy-phenyl)-ethenyl]-3-butyl-4-oxo-4H-pyrido[1,2-a]pyrimidine-7-carboxylic acid;

2-trans-[2-(2,5-dimethyl-phenyl)-ethenyl]-3-ethyl-4-oxo-4H-pyrido[1,2-a]pyrimidine-7-carboxylic acid; m.p. 298°-300° C.;

2-trans-[2-(2,5-dimethyl-phenyl)-ethenyl]-3-butyl-4-oxo-4H-pyrido[1,2-a]pyrimidine-7-carboxylic acid;

2-trans-[2-(2,3-dimethoxy-phenyl)-ethenyl]-3-ethyl-4-oxo-4H-pyrido]1,2-a]pyrimidine-7-carboxylic acid; m.p. 256°-258° C;

2-trans-[2-(2,3-dimethoxy-phenyl)-ethenyl]-3-butyl-4-oxo-4H-pyrido[1,2-a]pyrimidine-7-carboxylic acid; m.p. 258°-260° C.;

2-trans-[2-(2-methoxy-phenyl)-ethenyl]-3-ethyl-4-oxo-4H-pyrido[1,2-a]pyrimidine-7-carboxylic acid; m.p. 273°-275° C.;

2-trans-[2-(4-methoxy-phenyl)-ethenyl]-3-ethyl-4-oxo-
  4H-pyrido[1,2-a]pyrimidine-7-carboxylic acid; m.p.
  289°-291° C.;
2-trans-[2-(2,4-dimethyl-phenyl)-ethenyl]-3-ethyl-4-
  oxo-4H-pyrido[1,2-a]pyrimidine-7-carboxylic acid;
2-trans-[2-(2,3-diethoxy-phenyl)-ethenyl]-3-ethyl-4-oxo-
  4H-pyrido[1,2-a]pyrimidine-7-carboxylic acid;
2-trans-[2-(2-isopropoxy-phenyl)-ethenyl]-3-ethyl-4-
  oxo-4H-pyrido[1,2-a]pyrimidine-7-carboxylic acid;
2-trans-[2-(2-propoxy-phenyl)-ethenyl]-3-ethyl-4-oxo-
  4H-pyrido[1,2-a]pyrimidine-7-carboxylic acid;
2-trans-[2-(2-allyloxy-phenyl)-ethenyl]-3-ethyl-4-oxo-
  4H-pyrido[1,2-a]pyrimidine-7carboxylic acid;
2-trans-[2-(2-ethoxy-phenyl)-ethenyl]-3-butyl-4-oxo-
  4H-pyrido[1,2-a]pyrimidine-7-carboxylic acid;
2-trans-[2-(2-ethoxy-phenyl)-ethenyl]-3-ethyl-4-oxo-
  4H-pyrido[1,2-a]pyrimidine-7-carboxylic acid; m.p.
  265°-268° C.;
2-trans-[2-(2,5-dimethoxy-phenyl)-ethenyl]-3-ethyl-4-
  oxo-4H-pyrido[1,2-a]pyrimidine-7-carboxylic acid;
  m.p. 274°-276° C.;
2-trans-[2-(2,5-dimethoxy-phenyl)-ethenyl]-3-butyl-4-
  oxo-4H-pyrido[1,2-a]pyrimidine-7-carboxylic acid;
2-trans-[2-(2-methoxy-3-ethoxy-phenyl)-ethenyl]-3-
  ethyl-4-oxo-4H-pyrido[1,2-a]pyrimidine-7-carboxylic
  acid; m.p. 245°-247° C.;
2-trans-[2-(2-methoxy-3-ethoxy-phenyl)ethenyl]-3-
  butyl-4-oxo-4H-pyrido[1,2-a]pyrimidine-7-carboxylic
  acid; m.p. 213°-215° C.;
2-trans-[2-(2-ethoxy-3-methoxy-phenyl)-ethenyl]-3-
  ethyl-4-oxo-4H-pyrido[1,2-a]pyrimidine-7-carboxylic
  acid;
2-trans-[2-(2-ethoxy-3-methoxy-phenyl)-ethenyl]-3-
  butyl-4-oxo-4H-pyrido[1,2-a]pyrimidine-7-carboxylic
  acid;
2-trans-[2-(2-ethoxy-5-methoxy-phenyl)-ethenyl]-3-
  ethyl-4-oxo-4H-pyrido[1,2-a]pyrimidine-7-carboxylic
  acid;
2-trans-[2-(2-ethoxy-5-methoxy-phenyl)-ethenyl]-3-
  butyl-4-oxo-4H-pyrido[1,2-a]pyrimidine-7-carboxylic
  acid;
2-trans-[2-(2,3,4-trimethoxy-phenyl)-ethenyl]-3-ethyl-4-
  oxo-4H-pyrido[1,2-a]pyrimidine-7-carboxylic acid;
2-trans-[2-(2,3,4-trimethoxy-phenyl)-ethenyl]-3-butyl-4-
  oxo-4H-pyrido[1,2-a]pyrimidine-7-carboxylic acid;
2-trans-[2-(2,4,5-trimethoxy-phenyl)-ethenyl]-3-butyl-4-
  oxo-4-H-pyrido[1,2-a]pyrimidine-7-carboxylic acid;
2-trans-[2-(2-thienyl)-ethenyl]-3-ethyl-4-oxo-4H-
  pyrido[1,2-a]pyrimidine-7-carboxylic acid;
2-trans-[2-(2-thienyl)-ethenyl]-3-butyl-4-oxo-4H-
  pyrido[1,2-a]pyrimidine-7carboxylic acid;
2-trans-[2-(5-methyl-2-thienyl)-ethenyl]-3-ethyl-4-oxo-
  4H-pyrido[1,2-a]pyrimidine-7-carboxylic acid;
2-trans-[2-(5-methyl-2-thienyl)-ethenyl]-3-butyl-4-oxo-
  4H-pyrido[1,2-a]pyrimidine-7-carboxylic acid;
2-trans-[2-(2-pyridyl)-ethenyl]-3-ethyl-4-oxo-4H-
  pyrido[1,2-a]pyrimidine-7-carboxylic acid;
2-trans-[2-(2-pyridyl)-ethenyl]-3-butyl-4-oxo-4H-
  pyrido[1,2-a]pyrimidine-7-carboxylic acid;
2-trans-[2-(6-methyl-2-pyridyl)-ethenyl]-3-ethyl-4-oxo-
  4H-pyrido[1,2-a]pyrimidine-7-carboxylic acid;
2-trans-[2-(6-methyl-2-pyridyl)-ethenyl]-3-butyl-4-oxo-
  4H-pyrido[1,2-a]pyrimidine-7-carboxylic acid;
2-trans-[2-(5-methyl-2-furyl)-ethenyl]-3-butyl-4-oxo-
  4H-pyrido[1,2-a]pyrimidine-7-carboxylic acid.

EXAMPLE 5

6-amino-nicotinic acid (1.5 g) was reacted with ethyl 2-methyl-acetoacetate (3.3 g) in the presence of polyphosphoric acid (15 g, obtained from 7.2 g of $P_2O_5$ and 7.8 g of 99% $H_3PO_4$) under stirring at 100° C. for 8 hours. After cooling the reaction mixture was diluted in ice-water and the precipitate was filtered and thoroughly washed with water until neutral, so obtaining 2,3-dimethyl-4-oxo-4H-pyrido[1,2-a]pyrimidine-7-carboxylic acid; m.p. >280°dec.(1.8 g), which was reacted with benzaldehyde (3.5 g) in methanol (100 ml) in the presence of sodium methoxide (2.23 g) under stirring at reflux temperature for 96 hours.

After cooling the precipitate was filtered, washed with isopropyl ether and dissolved in water: acidification with acetic acid gave a precipitate which was filtered and crystallized from dioxane to give 1.2 g of 2-trans-(2-phenyl-ethenyl)-3-methyl-4-oxo-4H-pyrido[1,2-a]pyrimidine-7-carboxylic acid; m.p. 312°-313° C.

EXAMPLE 6

By proceeding according to Examples 1,3 and 5 starting from ethyl aceto-acetate and ethyl 2-methyl-acetoacetate, the following compounds were prepared:
2-trans-[2-(2-methyl-phenyl)-ethenyl]-4-oxo-4H-
  pyrido[1,2-a]pyrimidine-7-carboxylic acid; m.p.
  267°-269° C.;
2-trans-[2-(3-methyl-phenyl)-ethenyl]-4-oxo-4H-
  pyrido[1,2-a]pyrimidine-7-carboxylic acid; m.p.
  272°-274° C.;
2-trans-[2-(4-methyl-phenyl)-ethenyl]-4-oxo-4H-
  pyrido[1,2-a]pyrimidine-7-carboxylic acid; m.p.
  313°-315° C.;
2-trans-[2-(2-methoxy-phenyl)-ethenyl]-4-oxo-4H-
  pyrido[1,2-a]pyrimidine-7-carboxylic acid; m.p.
  263°-265° C.;
2-trans-[2-(3-methoxy-phenyl)-ethenyl]-4-oxo-4H-
  pyrido[1,2-a]pyrimidine-7-carboxylic acid; m.p.
  254°-260° C.;
2-trans-[2-(4-methoxy-phenyl)-ethenyl]-4-oxo-4H-
  pyrido[1,2-a]pyrimidine-7-carboxylic acid; m.p.
  300°-304° C.;
2-trans-[2-(3-chloro-phenyl)-ethenyl]-4-oxo-4H-
  pyrido[1,2-a]pyrimidine-7-carboxylic acid; m.p.
  297°-299° C.;
2-trans[2-(2-chloro-phenyl)-ethenyl]-4-oxo-4H-
  pyrido[1,2-a]pyrimidine-7-carboxylic acid; m.p.
  >270° C., IR $\nu(C=O)$ acid 1700 cm$^{-1}$ $\nu(C=O)$
  ketone 1675 cm$^{-1}$;
2-trans-[2-(4-chloro-phenyl)-ethenyl]-4-oxo-4H-
  pyrido[2,1-a]pyrimidine-7-carboxylic acid; m.p.
  >280° C., IR $\nu(C=O)$ acid 1710 cm$^{-1}$ $\nu(C=O)$
  ketone 1685 cm$^{-1}$;
2-trans-[2-(2,4-dichloro-phenyl)-ethenyl]-4-oxo-4H-
  pyrido[1,2-a]pyrimidine-7-carboxylic acid; m.p.
  >270° C., IR $\nu(C=O)$ acid 1715 cm$^{-1}$ $\nu(C=O)$
  ketone 1680 cm$^{-1}$;
2-trans-[2-(2,6-dichlorophenyl)-ethenyl]-4-oxo-4H-
  pyrido[1,2-a]pyrimidine-7-carboxylic acid; m.p.
  >265° C., IR $\nu(C=O)$ acid 1705 cm$^{-1}$ $\nu(C=O)$
  ketone 1670 cm$^{-1}$;
2-trans-[2-(3,4-dichlorophenyl)-ethenyl]-4-oxo-4H-
  pyrido[1,2-a]pyrimidine-7-carboxylic acid; m.p.
  255°(dec.), IR $\nu(C=O)$acid 1700 cm$^{-1}$, $\nu(C=O)$
  ketone 1675 cm$^{-1}$;

2-trans-[2-(3-hydroxy-phenyl)-ethenyl]-4-oxo-4H-pyrido[1,2-a]pyrimidine-7-carboxylic acid; m.p. 310°–320° C.(dec.);

2-trans-[2-(4-N,N-dimethylamino-phenyl)-ethenyl]-4-oxo-4H-pyrido[1,2-a]pyrimidine-7-carboxylic acid; m.p. 290°–300° C.(dec.);

2-trans-[2-(2,4-dimethyl-phenyl)-ethenyl]-4-oxo-4H-pyrido[1,2-a]pyrimidine-7-carboxylic acid; m.p. 312°–316° C.;

2-trans-[2-(2,5-dimethyl-phenyl)-ethenyl]-4-oxo-4H-pyrido[1,2-a]pyrimidine-7-carboxylic acid; m.p. 219°–222° C.;

2-trans-[2-(2,3-dimethoxy-phenyl)-ethenyl]-4-oxo-4H-pyrido[1,2-a]pyrimidine-7-carboxylic acid; m.p. 275°–280° C.;

2-trans-[2-(2,5-dimethoxy-phenyl)-ethenyl]-4-oxo-4H-pyrido[1,2-a]pyrimidine-7-carboxylic acid; m.p. 315°–319° C.;

2-trans-[2-(2,3,4-trimethoxy-phenyl)-ethenyl]-4-oxo-4H-pyrido[1,2-a]pyrimidine-7-carboxylic acid; m.p. 279°–280° C.;

2-trans-[2-(2-thienyl)-ethenyl]-4-oxo-4H-pyrido[1,2-a]pyrimidine-7-carboxylic acid;

2-trans-[2-(2-furyl)-ethenyl]-4-oxo-4H-pyrido[1,2-a]pyrimidine-7-carboxylic acid;

2-trans-[2-(2-methyl-phenyl)-ethenyl]-3-methyl-4-oxo-4H-pyrido[1,2-a]pyrimidine-7-carboxylic acid; m.p. 330°–333° C.;

2-trans-[2-(3-methyl-phenyl)-ethenyl]-3-methyl-4-oxo-4H-pyrido[1,2-a]pyrimidine-7-carboxylic acid; m.p. 294°–296° C.;

2-trans-[2-(4-methyl-phenyl)-ethenyl]-3-methyl-4-oxo-4H-pyrido[1,2-a]pyrimidine-7-carboxylic acid; m.p. 306°–308° C.;

2-trans-[2-(2-methoxy-phenyl)-ethenyl]-3-methyl-4-oxo-4H-pyrido[1,2-a]pyrimidine-7-carboxylic acid; m.p. 270°–272° C.;

2-trans-[2-(3-methoxy-phenyl)-ethenyl]-3-methyl-4-oxo-4H-pyrido[1,2-a]pyrimidine-7-carboxylic acid; m.p. 273°–274° C.;

2-trans-[2-(4-methoxy-phenyl)-ethenyl]-3-methyl-4-oxo-4H-pyrido[1,2-a]pyrimidine-7-carboxylic acid; m.p. 305°–307° C.;

2-trans-2-(2-chloro-phenyl)-ethenyl]-3-methyl-4-oxo-4H-pyrido[1,2-a]pyrimidine-7-carboxylic acid; m.p. 245°(dec.), IR $\nu$(C=O) acid 1710 cm$^{-1}$, $\nu$(C=O) ketone 1680, 1625 cm$^{-1}$;

2-trans-[2-(3-chloro-phenyl)-ethenyl]-3-methyl-4-oxo-4H-pyrido[1,2-a]pyrimidine-7-carboxylic acid; m.p. >280° C., IR $\nu$(C=O) acid 1720 cm$^{-1}$, $\nu$(C=O) ketone 1680, 1620 cm$^{-1}$;

2-trans-[2-(4-chloro-phenyl)-ethenyl]-3-methyl-4-oxo-4H-pyrido[1,2-a]pyrimidine-7-carboxylic acid, m.p. >280° C., IR $\nu$(C=O) acid 1710 cm$^{-1}$, $\nu$(C=O) ketone 1690, 1625 cm$^{-1}$;

2-trans-[2-(2,4-dichloro-phenyl)-ethenyl]-3-methyl-4-oxo-4H-pyrido[1,2-a]pyrimidine-7-carboxylic acid, m.p. >260° C., IR $\nu$(C=O) acid 1710 cm$^{-1}$, $\nu$(C=O) ketone 1680 cm$^{-1}$;

2-trans-[2-(2,6-dichlorophenyl)-ethenyl]-3-methyl-4-oxo-4H-pyrido[1,2-a]pyrimidine-7-carboxylic acid, m.p. 252°(dec.) IR $\nu$(C=O) acid 1700 cm$^{-1}$, $\nu$(C=O) ketone 1675 cm$^{-1}$;

2-trans-[2-(3,4-dichlorophenyl)-ethenyl]-3-methyl-4-oxo-4H-pyrido[1,2-a]pyrimidine-7-carboxylic acid, m.p. >260° C., IR $\nu$(C=O) acid 1705 cm$^{-1}$, $\nu$(C=O) ketone 1670 cm$^{-1}$;

2-trans-[2-(3-trifluoromethyl-phenyl)-ethenyl]-3-methyl-4-oxo-4H-pyrido[1,2-a]pyrimidine-7-carboxylic acid, IR $\nu$(C=O) acid 1720 cm$^{-1}$, $\nu$(C=O) ketone 1690 cm$^{-1}$;

2-trans-[2-(3-hydroxy-phenyl)-ethenyl]-3-methyl-4-oxo-4H-pyrido[1,2-a]pyrimidine-7-carboxylic acid;

2-trans[2-(4-hydroxy-phenyl)-ethenyl]-3-methyl-4-oxo-4H-pyrido[1,2-a]pyrimidine-7-carboxylic acid;

2-trans-[2-(4-N,N-dimethylamino-phenyl)-ethenyl]-3-methyl-4-oxo-4H-pyrido[1,2-a]pyrimidine-7-carboxylic acid;

2-trans-[2-(4-N,N-diethylamino-phenyl)-ethenyl]-3-methyl-4-oxo-4H-pyrido[1,2-a]pyrimidine-7-carboxylic acid;

2-trans-[2-(2,4-dimethyl-phenyl)-ethenyl]-3-methyl-4-oxo-4H-pyrido[1,2-a]pyrimidine-7-carboxylic acid, m.p. >280° C.;

2-trans-[2-(2,5-dimethyl-phenyl)-ethenyl]-3-methyl-4-oxo-4H-pyrido[1,2-a]pyrimidine-7-carboxylic acid, m.p. 308°–310° C.;

2-trans-[2-(2,3-dimethoxy-phenyl)-ethenyl]-3-methyl-4-oxo-4H-pyrido[1,2-a]pyrimidine-7carboxylic acid, m.p. 278°–279° C.;

2-trans-[2-(2,4-dimethoxy-phenyl)-ethenyl]-3-methyl-4-oxo-4H-pyrido[1,2-a]pyrimidine-7-carboxylic acid;

2-trans-[2-(2,5-dimethoxy-phenyl)-ethenyl]-3-methyl-4-oxo-4H-pyrido[1,2-a]pyrimidine-7-carboxylic acid, m.p. 265°–270° C. (dec.);

2-trans-[2-(3,4-dimethoxy-phenyl)-ethenyl]-3-methyl-4-oxo-4H-pyrido[1,2-a]pyrimidine-7-carboxylic acid, m.p. 308°–310° C.;

2-trans-[2-(3,5-dimethoxy-phenyl)-ethenyl]-3-methyl-4-oxo-4H-pyrido[1,2-a]pyrimidine-7-carboxylic acid;

2-trans-[2-(2,3,4-trimethoxy-phenyl)-ethenyl]-3-methyl-4-oxo-4H-pyrido[1,2-a]pyrimidine-7-carboxylic acid;

2-trans-[2-(2,4,5-trimethoxy-phenyl)-ethenyl]-3-methyl-4-oxo-4H-pyrido[1,2-a]pyrimidine-7-carboxylic acid;

2-trans-[2-(3,4,5-trimethoxy-phenyl)-ethenyl]-3-methyl-4-oxo-4H-pyrido[1,2-a]pyrimidine-7-carboxylic acid, m.p. 220°–230° C.(dec.);

2-trans-[2-(2-thienyl)-ethenyl]-3-methyl-4-oxo-4H-pyrido[1,2-a]pyrimidine-7-carboxylic acid, m.p. >280° C., IR $\nu$(C=O) acid 1705 cm$^{-1}$, $\nu$(C=O) ketone 1655, 1610 cm$^{-1}$;

2-trans-[2-(2-furyl)-ethenyl]-3-methyl-4-oxo-4H-pyrido[1,2-a]pyrimidine-7-carboxylic acid, m.p. $\nu$300° C., IR $\nu$(C=O) acid 1735 cm$^{-1}$, $\nu$(C=O) ketone 1655, 1615 cm$^{-1}$.

EXAMPLE 7

Trimethyl-sulphoxonium iodide (0.7 g) was reacted with 50% sodium hydride (0.15 g) in dimethylformamide (30 ml) under stirring at room temperature for 1 hour, then a solution of 2-trans-(2-phenyl-ethenyl)-3-ethyl-4-oxo-4H-pyrido[1,2-a]pyrimidine-7-carboxylic acid methyl ester, m.p. 214°–216° C., (0.82 g) in dimethyl-formamide (20 ml) was added. The mixture was allowed to react under stirring at room temperature for 3 hours, then it was diluted with ice water and filtered. Crystallization from acetone gave 2-trans-(2-phenyl-ethenyl)-3-ethyl-6,7-methylen-4-oxo-4H-pyrido[1,2-a]pyrimidine-7-carboxylic acid, methyl ester, m.p. 194°–195° C. (0.58 g), which was reacted with 1% KOH in 95% ethanol solution (11 ml) at reflux temperature for 15 minutes. After cooling the reaction mixture was acidified with acetic acid, concentrated in vacuo and diluted with ice water: the precipitate was filtered and washed with water until neutral. Crystallization from acetone gave 0.34 g of 2-trans-(2-phenyl-ethenyl)-3-ethyl-6,7-methylen-4-oxo-4H-pyrido[1,2]pyrimidine-7-carboxylic acid, m.p. 215°–216° C., NMR (CF$_3$COOD) δ: 1.22(m) and 2.93(m)(6,7-CH$_2$ protons), 1.36(t) (CH$_2$CH$_3$), 2.93(m)(CH$_2$—CH$_3$), 5.51(d.d)(C-6proton), 7.01(d) (C-9 proton), 7.31(d)(H$_\beta$ vinyl proton), 7.63(b.s)(phenyl protons), 7.76(d)(H$_\alpha$ vinyl proton), 8.26(d)(C-8 proton). By proceeding analogously the following compounds were prepared:

2-trans-(2-phenyl-ethenyl)-3-methyl-6,7-methylen-4-oxo-4H-pyrido[1,2-a]pyrimidine-7-carboxylic acid, m.p. 222°–224° C., NMR(CF$_3$COOD) δ: 1.18(t) and 2.84(d.d)(6,7 methylen protons), 5.44(d.d)(C-6 proton), 6.95(d)(C-9 proton), 8.18(d)(C-8 proton);

2-trans-(2-phenyl-ethenyl)-3-propyl-6,7-methylen-4-oxo-4H-pyrido[1,2-a]pyrimidine-7-carboxylic acid, m.p. 160° C.(dec.), NMR(CF$_3$COOD) δ: 1.13(t) (6,7-methylen proton and —CH$_2$CH$_2$CH$_3$), 1.60-2.00(m) (—CH$_2$CH$_2$CH$_3$), 2.76-3.02(m) (—CH$_2$CH$_2$CH$_3$), 5.47(d.d) (C-6 proton), 6.97(d) ( C-9 proton), 7.26(d) (H$_\beta$ vinyl proton), 7.38–7.80(m) (H$_\alpha$ vinyl proton and phenyl protons), 8.20(d) (C-8 proton);

2-trans-(2-phenyl-ethenyl)-6,7-methylen-4-oxo-4H-pyrido[1,2-a]pyrimidine-7-carboxylic acid, m.p. 205°–210° C.(dec.);

2-trans-(2-phenyl-ethenyl)-3-butyl-6,7-methylen-4-oxo-4H-pyrido[1,2-a]pyrimidine-7-carboxylic acid, m.p. 135° C.(dec.), NMR(CF$_3$COOD) δ: 1.00(m)(6,7-methylen proton), 2.90(m)(6,7-methylen proton and —CH$_2$—CH$_2$—CH$_2$—CH$_3$), 5.66(d.d)(C-6 proton), 6.95(d)(C-9 proton), 8.19(d) (C-8 proton);

2-trans-(2-phenyl-ethenyl)-3-pentyl-6,7-methylen-4-oxo-4H-pyrido[1,2-a]pyrimidine-7-carboxylic acid.

EXAMPLE 8

Trimethyl-sulphoxonium iodide (1 g) was reacted with 50% sodium hydride (0.22 g) in dimethylformamide (30 ml) under stirring at room temperature for 30 minutes, then a solution of 2-trans-[2-(3-methoxy-phenyl)-ethenyl]-3-ethyl-4-oxo-4H-pyrido[1,2-a]pyrimidine-7-carboxylic acid, methyl ester, m.p. 177°–179° C., (1.27 g) in dimethylformamide (20 ml) was added. The mixture was allowed to react under stirring at room temperature for 2 hours, then it was diluted with ice water and the precipitate was filtered, so obtaining 1.19 g of 2-trans-[2-(3-methoxy-phenyl)-ethenyl]-3-ethyl-6,7-methylen-4-oxo-4H-pyrido[1,2-a]pyrimidine-7-carboxylic acid, methyl ester (m.p. 184°–188° C.), which was treated with 0.5% KOH in 95% ethanol solution (40 ml) at reflux temperature for 15 minutes. After cooling the reaction mixture was diluted with water and acidified with acetic acid and the precipitate was filtered: crystallization from CH$_2$Cl$_2$/methanol gave 2-trans-[2-(3-methoxy-phenyl)-ethenyl]-3-ethyl-6,7-methylen-4-oxo-4H-pyrido[1,2-a]pyrimidine-7-carboxylic acid (0.65 g), m.p. 184°–188° C. NMR (CF$_3$COOD) δ: 1.22(d.d) (one of 6,7-methylen protons), 1.36(t) (—CH$_2$—CH$_3$), 2,96(m)(—CH$_2$CH$_3$ and 6,7-methylen proton), 4.12(s) (OCH$_3$), 5.50(d.d) (c-6 proton), 7.03(d) (c-9 proton), 7.36(d) (H$_\beta$-vinyl proton), 7.68(d) (H$_\alpha$-vinyl proton), 7.18–7.70(m) (4-phenyl protons), 8.26(d) (c-8 proton), J$_{H\alpha H\beta}$=16 Hz.

By proceeding analogously, the following compounds were prepared:

2-trans-[2-(2-methyl-phenyl)-ethenyl]-3-ethyl-6,7-methylen-4-oxo-4H-pyrido[1,2-a]pyrimidine-7-carboxylic acid; m.p. 225°–227° C.;

2-trans-[2-(3-methyl-phenyl)-ethenyl]-3-ethyl-6,7-methylen-4-oxo-4H-pyrido[1,2-a]pyrimidine-7-carboxylic acid; m.p. 165° C.(dec.);

2-trans-[2-(3-methyl-phenyl)-ethenyl]-3-propyl-6,7-methylen-4-oxo-4H-pyrido[1,2-a]pyrimidine-7-carboxylic acid; m.p. 140° C.(dec.);

2-trans-[2-(4-fluoro-phenyl)-ethenyl]-3-ethyl-6,7-methylen-4-oxo-4H-pyrido[1,2-a]pyrimidine-7-carboxylic acid;

2-trans-[2-(4-fluoro-phenyl)-ethenyl]-3-propyl-6,7-methylen-4-oxo-4H-pyrido[1,2-a]pyrimidine-7-carboxylic acid;

2-trans-[2-(4-methyl-phenyl)-ethenyl]-3-ethyl-6,7-methylen-4-oxo-4H-pyrido[1,2-a]pyrimidine-7-carboxylic acid; m.p. 225°–235° C.(dec.);

2-trans-[2-(4-methyl-phenyl)-ethenyl]-3-propyl-6,7-methylen-4-oxo-4H-pyrido[1,2-a]pyrimidine-7-carboxylic acid; m.p. 140°–150° C.(dec.);

2-trans-[2-methoxy-phenyl)-ethenyl]-3-ethyl-6,7-methylen-4-oxo-4H-pyrido[1,2-a]pyrimidine-7-carboxylic acid; m.p. 208°–210° C.;

2-trans-[2-(2-methoxy-phenyl)-ethenyl]-3-propyl-6,7-methylen-4-oxo-4H-pyrido[1,2-a]pyrimidine-7-carboxylic acid; m.p. 130° C.(dec.);

2-trans-[2-(2-methyl-phenyl)-ethenyl]-3-propyl-6,7-methylen-4-oxo-4H-pyrido[1,2-a]pyrimidine-7-carboxylic acid, m.p. 140° C.(dec.) NMR (CF$_3$COOD) δ: 1.12(m) (6,7-methylen proton and —CH$_2$CH$_2$CH$_3$), 1.73(m) (—CH$_2$CH$_2$CH$_3$), 2.47(s) (—CH$_3$), 2.87(m) (6,7-methylen proton and —CH$_2$CH$_2$CH$_3$), 5.46(d.d) (C-6 proton), 6.94(d) (C-9 proton), 7.16(d) (H$_\beta$-vinyl proton), 7.96(d) (H$_\alpha$-vinyl proton) 8.19(d) (C-8 proton), J$_{H\alpha H\beta}$=16 Hz.

2-trans-[2-(3-methoxy-phenyl)-ethenyl]-3-propyl-6,7-methylen-4-oxo-4H-pyrido[1,2-a]pyrimidine-7-carboxylic acid; m.p. 130° C.(dec.), NMR (CF$_3$COOD) δ: 1.13(m) (6,7-methylen proton and —CH$_2$CH$_2$CH$_3$), 2.88(m) (6,7-methylen proton and —CH$_2$CH$_2$CH$_3$), 5.46(d.d) (C-6 proton), 6.97(d) (C-9 proton), 7.18 (d) (H$_\beta$-vinyl proton), 7.64(d) (H$_\alpha$-vinyl proton), 8.21(d) (C-8 proton), J$_{H\alpha H\beta}$=16 Hz;

2-trans-[2-(3-ethoxy-phenyl)-ethenyl]-3-ethyl-6,7-methylen-4-oxo-4H-pyrido[1,2-a]pyrimidine-7-carboxylic acid; m.p. 188°–190° C.;

2-trans-[2-(3-ethoxy-phenyl)-ethenyl]-3-propyl-6,7-methylen-4-oxo-4H-pyrido[1,2-a]pyrimidine-7-carboxylic acid; m.p. 97°–102° C.(dec.);

2-trans-[2-(2,3-dimethoxy-phenyl)-ethenyl]-3-ethyl-6,7-methylen-4-oxo-4H-pyrido[1,2-a]pyrimidine-7-carboxylic acid; m.p. 188°–190° C.;

2-trans-[2-(2,3-dimethoxy-phenyl)-ethenyl]-3-propyl-6,7-methylen-4-oxo-4H-pyrido[1,2-a]pyrimidine-7-carboxylic acid; m.p. 100°–110° C.(dec.);

2-trans-[2-(2,5-dimethoxy-phenyl)-ethenyl]-3-propyl-6,7-methylen-4-oxo-4H-pyrido[1,2-a]pyrimidine-7-carboxylic acid; m.p. 170°–173° C. NMR (CF$_3$COOD) δ: 1.20(m) (6,7-methylene proton), 2.89(m) (6,7-methylen proton and —CH$_2$CH$_2$CH$_3$), 5.48(d.d) (C-6 proton), 7.00(d) (C-9 proton), 7.45(d) (H$_\beta$-vinyl proton), 7.98(d) (H$_\alpha$-vinyl proton), 8.22(d) (C-8 proton), J$_{H\alpha H\beta}$=16 Hz;

2-trans-[2-(2,5-dimethoxy-phenyl)-ethenyl]-3-ethyl-6,7-methylen-4-oxo-4H-pyrido[1,2-a]pyrimidine-7-carboxylic acid; m.p. 192°–195° C.;

2-trans-[2-(2-methoxy-3-ethoxy-phenyl)-ethenyl]-3-ethyl-6,7-methylen-4-oxo-4H-pyrido[1,2-a]pyrimidine-7-carboxylic acid; m.p. 180°–185° C.(dec.);

2-trans-[2-(2-methoxy-3-ethoxy-phenyl)-ethenyl]-3-propyl-6,7-methylen-4-oxo-4H-pyrido[1,2-a]pyrimidine-7-carboxylic acid; m.p. 141°–143° C.;

2-trans-[2-(2-ethoxy-3-methoxy-phenyl)-ethenyl]-3-ethyl-6,7-methylen-4-oxo-4H-pyrido[1,2-a]pyrimidine-7-carboxylic acid;

2-trans-[2-(2-ethoxy-3-methoxy-phenyl)-ethenyl]-3-propyl-6,7-methylen-4-oxo-4H-pyrido[1,2-a]pyrimidine-7-carboxylic acid; m.p. 181°–183° C.;

2-trans-[2-(2-ethoxy-5-methoxy-phenyl)-ethenyl]-3-ethyl-6,7-methylen-4-oxo-4H-pyrido[1,2-a]pyrimidine-7-carboxylic acid;

2-trans-[2-(2-ethoxy-5-methoxy-phenyl)-ethenyl]-3-propyl-6,7-methylen-4-oxo-4H-pyrido[1,2-a]pyrimidine-7-carboxylic acid;

2-trans-[2-(2,3,4-trimethoxy-phenyl)-ethenyl]-3-ethyl-6,7-methylen-4-oxo-4H-pyrido[1,2-a]pyrimidine-7-carboxylic acid;

2-trans-[2-(2,3,4-trimethoxy-phenyl)-ethenyl]-3-propyl-6,7-methylen-4-oxo-4H-pyrido[1,2-a]pyrimidine-7-carboxylic acid;

2-trans-[2-(2,4,5-trimethoxy-phenyl)-ethenyl]-3-ethyl-6,7-methylen-4-oxo-4H-pyrido[1,2-a]pyrimidine-7-carboxylic acid;

2-trans-[2-(2,4,5-trimethoxy-phenyl)-ethenyl]-3-propyl-6,7-methylen-4-oxo-4H-pyrido[1,2-a]pyrimidine-7-carboxylic acid; m.p. 224°–226° C.;

2-trans-[2-(3,4,5-trimethoxy-phenyl)-ethenyl]-3-ethyl-6,7-methylen-4-oxo-4H-pyrido[1,2-a]pyrimidine-7-carboxylic acid;

2-trans-[2-(3,4,5-trimethoxy-phenyl)-ethenyl]-3-propyl-6,7-methylen-4-oxo-4H-pyrido[1,2-a]pyrimidine-7-carboxylic acid;

2-trans-[2-(2,4-dimethyl-phenyl)-ethenyl]-3-propyl-6,7-methylen-4-oxo-4H-pyrido[1,2-a]pyrimidine-7-carboxylic acid; m.p. 184°–186° C.;

2-trans-[2-(3,4-dimethoxy-phenyl)-ethenyl]-3-propyl-6,7-methylen-4-oxo-4H-pyrido[1,2-a]pyrimidine-7-carboxylic acid; m.p. 208°–209° C.;

2-trans-[2-(4-methoxy-phenyl)-ethenyl]-3-propyl-6,7-methylen-4-oxo-4H-pyrido[1,2-a]pyrimidine-7-carboxylic acid; m.p. 180°–190° C.(dec.);

2-trans-[2-(4-methoxy-phenyl)-ethenyl]-3-ethyl-6,7-methylen-4-oxo-4H-pyrido[1,2-a]pyrimidine-7-carboxylic acid; m.p. 235°–237° C.;

2-trans-[2-(2-ethoxy-phenyl)-ethenyl]-3-propyl-6,7-methylen-4-oxo-4H-pyrido[1,2-a]pyrimidine-7-carboxylic acid; m.p. 178°–180° C;

2-trans-[2-(3,5-dimethoxy-phenyl)-ethenyl]-3-propyl-6,7-methylen-4-oxo-4H-pyrido[1,2-a]pyrimidine-7-carboxylic acid; m.p. 170°–180° C.(dec.);

2-trans-[2-(2,5-dimethyl-phenyl)-ethenyl]-3-propyl-6,7-methylen-4-oxo-4H-pyrido[1,2-a]pyrimidine-7-carboxylic acid; m.p. 150° C.(dec.);

2-trans-[2-(2,4-dimethyl-phenyl)-ethenyl]-3-ethyl-6,7-methylen-4-oxo-4H-pyrido[1,2-a]pyrimidine-7-carboxylic acid;

2-trans-[2-(2,5-dimethyl-phenyl)-ethenyl]-3-ethyl-6,7-methylen-4-oxo-4H-pyrido[1,2-a]pyrimidine-7carboxylic acid; m.p. 205°–207° C.;

2-trans-[2-(2-methyl-phenyl)-ethenyl]-3-butyl-6,7-methylen-4-oxo-4H-pyrido[1,2-a]pyrimidine-7-carboxylic acid; m.p. 240° C.(dec.);

2-trans-[2-(3-methoxy-phenyl)-ethenyl]-3-butyl-6,7-methylen-4-oxo-4H-pyrido[1,2-a]pyrimidine-7-carboxylic acid; m.p. 156°–158° C.;

2-trans-[2-(2,3-dimethoxy-phenyl)-ethenyl]-3-butyl-6,7-methylen-4-oxo-4H-pyrido[1,2-a]pyrimidine-7-carboxylic acid; m.p. 197°–198° C.;

2-trans-[2-(2-methoxy-3-ethoxy-phenyl)-ethenyl]-3-butyl-6,7-methylen-4-oxo-4H-pyrido[1,2-a]pyrimidine-7-carboxylic acid; m.p. 155°–157° C.;

2-trans-[2-(2,3-diethoxy-phenyl)-ethenyl]-3-propyl-6,7-methylen-4-oxo-4H-pyrido[1,2-a]pyrimidine-7-carboxylic acid; m.p. 177°–179° C.

EXAMPLE 9

By proceeding according to Example 8, starting from suitable 2-heteroaryl-ethenyl-derivatives, the following compounds were prepared:

2-trans-[2-(2-thienyl)-ethenyl]-3-ethyl-6,7-methylen-4-oxo-4H-pyrido[1,2-a]pyrimidine-7-carboxylic acid;

2-trans-[2-(2-thienyl)-ethenyl]-3-propyl-6,7-methylen-4-oxo-4H-pyrido[1,2-a]pyrimidine-7-carboxylic acid; m.p. 157°–162° C.(dec.);

2-trans-[2-(2-pyridyl)-ethenyl]-3-ethyl-6,7-methylen-4-oxo-4H-pyrido[1,2-a]pyrimidine-7-carboxylic acid;

2-trans-[2-(2-pyridyl)-ethenyl]-3-propyl-6,7-methylen-4-oxo-4H-pyrido[1,2-a]pyrimidine-7-carboxylic acid;

2-trans-[2-(5-methyl-2-thienyl)-ethenyl]-3-ethyl-6,7-methylen-4-oxo-4H-pyrido[1,2-a]pyrimidine-7-carboxylic acid;

2-trans-[2-(5-methyl-2-thienyl)-ethenyl]-3-propyl-6,7-methylen-4-oxo-4H-pyrido[1,2-a]pyrimidine-7-carboxylic acid;

2-trans-[2-(5-methyl-2-furyl)-ethenyl]-3-ethyl-6,7-methylen-4-oxo-4H-pyrido[1,2-a]pyrimidine-7-carboxylic acid;

2-trans-[2-(5-methyl-2-furyl)-ethenyl]-3-propyl-6,7-methylen-4-oxo-4H-pyrido[1,2-a]pyrimidine-7-carboxylic acid;

2-trans-[2-(6-methyl-2-pyridyl)-ethenyl]-3-ethyl-6,7-methylen-4-oxo-4H-pyrido[1,2-a]pyrimidine-7-carboxylic acid;

2-trans-[2-(6-methyl-2-pyridyl)-ethenyl]-3-propyl-6,7-methylen-4-oxo-4H-pyrido[1,2-a]pyrimidine-7-carboxylic acid.

EXAMPLE 10

By proceeding according to Examples 8 and 9, starting from suitable 2-aryl-ethenyl- and 2-heteroaryl-ethenyl-derivatives, the following compounds were prepared:

2-trans-[2-(2-methyl-phenyl)-ethenyl]-6,7-methylen-4-oxo-4H-pyrido[1,2-a]pyrimidine-7-carboxylic acid; m.p. 179°–182° C.;

2-trans-[2-(3-methyl-phenyl)-ethenyl]-6,7-methylen-4-oxo-4H-pyrido[1,2-a]pyrimidine-7-carboxylic acid; m.p. 272°–274° C.;

2-trans-[2-(4-methyl-phenyl)-ethenyl]-6,7-methylen-4-oxo-4H-pyrido[1,2-a]pyrimidine-7-carboxylic acid; m.p. 190°–194° C.;

2-trans-[2-(2-methoxy-phenyl)-ethenyl]-6,7-methylen-4-oxo-4H-pyrido[1,2-a]pyrimidine-7-carboxylic acid; m.p. 150° C.(dec.);

2-trans-[2-(3-methoxy-phenyl)-ethenyl]-6,7-methylen-4-oxo-4H-pyrido[1,2-a]pyrimidine-7-carboxylic acid; m.p. 204° C.(dec.);

2-trans-[2-(4-methoxy-phenyl)-ethenyl]-6,7-methylen-4-oxo-4H-pyrido[1,2-a]pyrimidine-7-carboxylic acid; m.p. 95°–110° C.(dec.);

2-trans-[2-(3-chloro-phenyl)-ethenyl]-6,7-methylen-4-oxo-4H-pyrido[1,2-a]pyrimidine-7-carboxylic acid; m.p. 205°–210° C.(dec.);

2-trans-[2-(3-hydroxy-phenyl)-ethenyl]-6,7-methylen-4-oxo-4H-pyrido[1,2-a]pyrimidine-7-carboxylic acid;

2-trans-[2-(4-N,N-dimethylamino-phenyl)-ethenyl]-6,7-methylen-4-oxo-4H-pyrido[1,2-a]pyrimidine-7-carboxylic acid;

2-trans-[2-(2,4-dimethyl-phenyl)-ethenyl]-6,7-methylen-4-oxo-4H-pyrido[1,2-a]pyrimidine-7-carboxylic acid; m.p. 199°–202° C.;

2-trans-[2-(2,5-dimethyl-phenyl)-ethenyl]-6,7-methylen-4-oxo-4H-pyrido[1,2-a]pyrimidine-7-carboxylic acid; m.p. 195°–200° C.;

2-trans-[2-(2,3-dimethoxy-phenyl)-ethenyl]-6,7-methylen-4-oxo-4H-pyrido[1,2-a]pyrimidine-7-carboxylic acid;

2-trans-[2-(2,5-dimethoxy-phenyl)-ethenyl]-6,7-methylen-4-oxo-4H-pyrido[1,2-a]pyrimidine-7-carboxylic acid;

2-trans-[2-(2,3,4-trimethoxy-phenyl)-ethenyl]-6,7-methylene-4-oxo-4H-pyrido[1,2-a]pyrimidine-7-carboxylic acid; m.p. 180°–182° C.;

2-trans-[2-(2-thienyl)-ethyl]-6,7-methylen-4-oxo-4H-pyrido[1,2-a]pyrimidine-7-carboxylic acid;

2-trans[2-(2-furyl)-ethenyl]-6,7-methylen-4-oxo-4H-pyrido[1,2-a]pyrimidine-7-carboxylic acid;

2-trans-[2-(2-methyl-phenyl)-ethenyl]-3-methyl-6,7-methylen-4-oxo-4H-pyrido[1,2-a]pyrimidine-7-carboxylic acid; m.p. 240° C.(dec.

2-trans-[2-(3-methyl-phenyl)-ethenyl]-3-methyl-6,7-methylen-4-oxo-4H-pyrido[1,2-a]pyrimidine-7-carboxylic acid; m.p. 190°–205° C.(dec.)

2-trans-[2-(4-methyl-phenyl)-ethenyl]-3-methyl-6,7-methylen-4-oxo-4H-pyrido[1,2-a]pyrimidine-7-carboxylic acid; m.p. 260°–265° C.(dec.)

2-trans-[2-(2-methoxy-phenyl)-ethenyl]-3-methyl-6,7-methylen-4-oxo-4H-pyrido[1,2-a]pyrimidine-7-carboxylic acid; m.p. 200°–205° C.(dec.);

2-trans-[2-(3-methoxy-phenyl)-ethenyl]-3-methyl-6,7-methylen-4-oxo-4H-pyrido[1,2-a]pyrimidine-7-carboxylic acid; m.p. 200°–205° C.(dec.)

2-trans-[2-(4-methoxy-phenyl)-ethenyl]-3-methyl-6,7-methylen-4-oxo-4H-pyrido[1,2-a]pyrimidine-7-carboxylic acid; m.p. 234°–238° C.;

2-trans-[2-(2-chloro-phenyl)-ethenyl]-3-methyl-6,7-methylen-4-oxo-4H-pyrido[1,2-a]pyrimidine-7-carboxylic acid;

2-trans-[2-(3-chloro-phenyl)-ethenyl]-3-methyl-6,7-methylen-4-oxo-4H-pyrido[1,2-a]pyrimidine-7 -carboxylic acid;

2-trans-[2-(4-chloro-phenyl)-ethenyl]-3-methyl-6,7-methylen-4-oxo-4H-pyrido[1,2-a]pyrimidine-7-carboxylic acid;

2-trans-[2-(3-hydroxy-phenyl)-ethenyl]-3-methyl-6,7-methylen-4-oxo-4H-pyrido[1,2-a]pyrimidine-7-carboxylic acid;

2-trans-[2-(4-hydroxy-phenyl)-ethenyl]-3-methyl-6,7-methylen-4-oxo-4H-pyrido[1,2-a]pyrimidine-7-carboxylic acid;

2-trans-[2-(4-N,N-dimethylamino-phenyl)-ethenyl]-3-methyl-6,7-methylen-4-oxo-4H-pyrido[1,2-a]pyrimidine-7-carboxylic acid;

2-trans-[2-(4-N,N-diethylamino-phenyl)-ethenyl]-3-methyl-6,7-methylen-4-oxo-4H-pyrido[1,2-a]pyrimidine-7-carboxylic acid;

2-trans-[2-(2,4-dimethyl-phenyl)-ethenyl]-3-methyl-6,7-methylen-4-oxo-4H-pyrido[1,2-a]pyrimidine-7-carboxylic acid; m.p. 220°–223° C.(dec.);

2-trans-[2-(2,5-dimethyl-phenyl)-ethenyl]-3-methyl-6,7-methylen-4-oxo-4-H-pyrido[1,2-a]pyrimidine-7-carboxylic acid, m.p. 235°–240° C. (dec.);

2-trans-[2-(2,3-dimethoxy-phenyl)-ethenyl]-3-methyl-6,7-methylen-4-oxo-4H-pyrido[1,2-a]pyrimidine-7-carboxylic acid, m.p. 207°–209° C.(dec.);

2-trans-[2-(2,4-dimethoxy-phenyl)-ethenyl]-3-methyl-6,7-methylen-4-oxo-4H-pyrido[1,2-a]pyrimidine-7-carboxylic acid;

2-trans-2-(2,5-dimethoxy-phenyl)-ethenyl]-3-methyl-6,7-methylen-4-oxo-4H-pyrido[1,2-a]pyrimidine-7-carboxylic acid, m.p. 171°–174° C.(dec.);

2-trans-[2-(3,4-dimethoxy-phenyl)-ethenyl]-3-methyl-6,7-methylen-4-oxo-4H-pyrido[1,2-a]pyrimidine-7-carboxylic acid, m.p. 207°–210° C.(dec.);

2-trans-[2-(3,5-dimethoxy-phenyl)-ethenyl]-3-methyl-6,7-methylen-4-oxo-4H-pyrido[1,2-a]pyrimidine-7-carboxylic acid;

2-trans-[2-(2,3,4-trimethoxy-phenyl)-ethenyl]-3-methyl-6,7-methylen-4-oxo-4H-pyrido[1,2-a]pyrimidine-7-carboxylic acid;

2-trans-[2-(2,4,5-trimethoxy-phenyl)-ethenyl]-3-methyl-6,7-methylen-4-oxo-4H-pyrido[1,2-a]pyrimidine-7carboxylic acid;

2-trans-[2-(3,4,5-trimethoxy-phenyll)-ethenyl]-3-methyl-6,7-methylen-4-oxo-4H-pyrido[1,2-a]pyrimidine-7-carboxylic acid; m.p. 175°–180° C.(dec.);

2-trans-[2-(2-thienyl)-ethenyl]-3- methyl-6,7-methylen-4-oxo-4H-pyrido[1,2-a]pyrimidine-7-carboxylic acid; m.p. 208°–211° C.(dec.);

2-trans-[2-(2-furyl)-ethenyl]-3-methyl-6,7-methylen-4-oxo-4-H-pyrido[1,2-a]pyrimidine-7-carboxylic acid.

EXAMPLE 11

2-methyl-3-propyl-7-(4,4-dimethyl-$\Delta^2$-oxazol-2-yl)-4-oxo-4H-pyrido[1,2-a]pyrimidine (3 g) (obtained according to J. Org. Chem., 1974,39, 2787) was reacted with ortho-tolualdbeide (6.3 g) in methanol (100 ml) in the presence of sodium methoxide (1.6 g), under stirring at reflux temperature for 120 hours. After cooling the reaction mixture was concentrated in vacuo and diluted with ice water: the precipitate was extracted with ethyl acetate and the solution was evaporated to dryness. Crystallization from methanol gave 2-trans-[2-(2-methyl-phenyl)-ethenyl]-3-propyl-7-(4,4-dimethyl-$\Delta^2$-oxazol-2-yl)-4-oxo-4H-pyrido[1,2-a]pyrimidine, m.p. 190°–191° C., (2 g), which was treated with HCl N/10 (10 ml) at room temperature for 1 hour; after neutralization with NaHCO$_3$, the precipitate was filtered and crystallized from methanol to give 1,1 g of 2-trans-[2-(2-methyl-phenyl)-ethenyl]-3-propyl-4-oxo-4H-pyrido[1,2-a]pyrimidine-7-carboxylic acid, m.p. 258°–259° C.

EXAMPLE 12

2-trans-[2-(2-methyl-phenyl)-ethenyl]-3-propyl-7-(4,4-dimethyl-$\Delta^2$-oxazol-2-yl)-4-oxo-4H-pyrido[1,2-a]pyrimidine (2 g), prepared according to Example 11, was added to a solution obtained reacting trimethyl-sulphoxonium iodide (1.32 g) and sodium hydride (0.15 g) in dimethylformamide (20 ml) for 2 hours. After 1 hour the reaction mixture was diluted with ice water and extracted with ethyl acetate: the solution was evaporated to dryness and the residue was crystallized from isopropyl alcohol, so obtained 1.1 g of 2- trans-[2-(2-methyl-phenyl)-ethenyl]-3-propyl-6,7-methylen-7-(4,4-dimethyl-$\Delta^2$-oxazol-2-yl)-4-oxo-4H-pyrido[1,2-a]pyrimidine, m.p. 107°–108° C., NMR(CDCl$_3$) δ:

0.76(t) and 2.26(d.d) (6,7-methylen protons), 4.99(d.d) (C-6 proton), 6.38(d) (C-9proton), 7.13(d) (H$_\beta$vinyl proton), 8.17(d) (H$_\alpha$vinyl proton, J$_{H\alpha H\beta}$=16 Hz, which were dissolved in dioxane (20 ml) and treated with a solution of oxalic acid (0.9 g) in water (10 ml) for 90 minutes. After neutralization with NaHCO$_3$ and dilution with ice water the precipitate was filtered: washing with methanol gave 0.5 g of 2-trans-[2-(2-methyl-phenyl)-ethenyl]-3-propyl-6,7-methylen-4-oxo-4H-pyrido[1,2-a]pyrimidine-7carboxylic acid; m.p. 140° C.(dec.).

EXAMPLE 13

2-trans-[2-(2-methyl-phenyl)-ethenyl]-3-propyl-4-oxo-4H-pyrido[1,2-a]pyrimidine-7-carboxylic acid (1,2 g) was reacted with thionyl chloride (0.6 ml) in dioxane (12) at reflux temperature for 1 hour, then the mixture was evaporated to dryness in vacuo. The residue was reacted with excess methanol at 50° C. for 30 minutes, then the solution was concentrated in vacuo and the residue diluted with ice water. Filtration of the precipitate gave 1.2 g of 2-trans-[2-(2-methyl-phenyl)-ethenyl]-3-propyl-4-oxo-4H-pyrido[1,2-a]pyrimidine-7 -carboxylic acid, methyl ester, m.p. 190°-193° C.

By proceeding analogously the following compounds were prepared:
2-trans-(2-phenyl-ethenyl)-3-propyl-4-oxo-4H-pyrido[1,2-a]pyridmidine-7-carboxylic acid, methyl ester, m.p. 222°-225° C.;
2-trans-(2-phenyl-ethenyl)-3-butyl-4-oxo-4H-pyrido[1,2-a]pyrimidine-7-carboxylic acid, methyl ester, m.p. 191°-193° C.;
2-trans[2-(2,5-dimethoxy-phenyl)-ethenyl]-3-propyl-4-oxo-4H-pyrido[1,2-a]pyrimidine-7-carboxylic acid, methyl ester, m.p. 197°-198° C.

EXAMPLE 14

2-trans-(2-phenyl-ethenyl)-3-methyl-6,7-methylen-4-oxo-4H-pyrido[1,2-a]pyrimidine-7-carboxylic acid (0.8 g) was reacted with methyl iodide (0.55 g) and anhydrous K$_2$CO$_3$(0.65 g) in dmethylformamide (7 ml) under stirring at room temperature for 4 hours. After dilution with ice water the precipitate was filtered off: crystallization from acetone gave 0.5 g of 2-trans-(2-phenyl-ethenyl)-3-methyl-6,7-methylen-4-oxo-4H-pyrido[1,2-a]pyrimidine-7-carboxylic acid, methyl ester, m.p. 164°-165° C. By proceeding analogously the following compound were prepared:
2-trans-(2-phenyl-ethenyl)-3-ethyl-6,7-methylen-4-oxo-4H-pyrido[1,2-a]pyrimidine-7carboxylic acid, methyl ester, m.p. 194°-195° C.;
2-trans-(2-phenyl-ethenyl)-3-butyl-6,7-methylen-4-oxo-4H-pyrido[1,2-a]pyrimidine-7-carboxylic acid, methyl ester, m.p. 112°-113° C.;
2-trans-[2-(2-methyl-phenyl)-ethenyl]-3-propyl-4-oxo-4H-pyrido[1,2-a]pyrimidine-7-carboxylic acid, methyl ester, m.p. 190°-193° C.;
2-trans-[2-(2-methoxy-3-ethoxy-phenyl)-ethenyl]-3-propyl-4-oxo-4H-pyrido[1,2-a]pyrimidine-7-carboxylic acid, methyl ester, m.p. 164°-166° C.;
2-trans-(2-phenyl-ethenyl)-3-methyl-4-oxo-4H-pyrido[1,2-a]pyrimidine-7-carboxylic acid, methyl ester, m.p. 220°-221° C.;
2-trans-[2-(2,5-dimethoxy-phenyl)-ethenyl]-3-propyl-6,7-methylen-4-oxo-4H-pyrido[1,2-a]pyrimidine-7carboxylic acid, methyl ester, m.p. 117°-120° C.;
2-trans-[-2-(3-methoxy-phenyl)-ethenyl]-3-ethyl-6,7-methylen-4-oxo-4H-pyrido[1,2-a]pyrimidine-7-carboxylic acid, methyl ester, m.p. 143°-146° C.

EXAMPLE 15

By proceeding according to Examples 13 and 14, using ethanol or Ethyl iodide resp., the following compounds were prepared:
2-trans-(2-phenyl-ethenyl)-3-propyl-4-oxo-4H-pyrido 1,2-a pyrimidine-7-carboxylic acid, ethyl ester;
2-trans-[2-(2- methyl-phenyl)-ethenyl]-3-propyl-4-oxo-4H-pyrido[1,2-a]pyrimidine-7-carboxylic acid, ethyl ester;
2-trans-(2-phenyl-ethenyl)-3-ethyl-6,7-methylen-4-oxo-4H-pyrido[1,2-a]pyrimidine-7-carboxylic acid, ethyl ester;
2-trans-[2-(2-methyl-phenyl)-ethenyl]-3-ethyl-6,7-methylen-4-oxo-4H-pyrido[1,2-a]pyrimidine-7-carboxylic acid, ethyl ester;
2-trans-(2-phenyl-ethenyl)-3-methyl-4-oxo-4H-pyrido[1,2-a]pyrimidine-7-carboxylic acid, ethyl ester, m.p. 194°-195° C.;
2-trans-[2-(2,3-dimethoxy-phenyl)-ethenyl]-3-ethyl-4-oxo-4-H-pyrido[1,2-a]pyrimidine-7-carboxylic acid, ethyl ester, m.p. 181°-183° C;
2-trans-[2-(3-methoxy-phenyl)-ethenyl]-3-ethyl-6,7-methylen-4-oxo-4H-pyrido[1,2-a]pyrimidine-7-carboxylic acid, ethyl ester;
2-trans-[2-(2-methyl-phenyl)-ethenyl]-3-propyl-6,7-methylen4-oxo-4H-pyrido[1,2-a]pyrimidine-7-carboxylic acid, ethyl ester.

EXAMPLE 16

By proceeding according to Examples 13 and 14 the isopropyl, n-hexyl and n-octyl esters of the following compounds were obtained;
2-trans-[2-(2-methyl-phenyl)-ethenyl]-3-propyl-4-oxo-4H-pyrido[1,2-a]pyrimidine-7-carboxylic acid;
2-trans-(2-pheny-ethenyl)-3-ethyl-6,7-methylen-4-oxo-4H-pyrido[1,2-a]pyrimidine-7carboxylic acid;
2-trans-[2-(2-methyl-phenyl)-ethenyl]-3-ethyl-6,7-methylen-4-oxo-4H-pyrido[1,2-a]pyrimidine-7-carboxylic acid;
2-trans-[2-(2-methyl-phenyl)-ethenyl]-3-propyl-6,7-methylen-4-oxo-4H-pyrido[1,2-a]pyrimidine-7-carboxylic acid;
2-trans-(2-phenyl-ethenyl)-3-methyl-4-oxo-4H-pyrido[1,2-a]pyrimidine-7-carboxylic acid;
2-trans-[2-(2,3-dimethoxy-phenyl)-ethenyl]-3-ethyl-4-oxo-4H-pyrido[1,2-a]pyrimidine-7-carboxylic acid;
2-trans-[2-(3-methoxy-phenyl)-ethenyl]-3-ethyl-6,7-methylen-4-oxo-4H-pyrido[1,2-a]pyrimidine-7-carboxylic acid.

EXAMPLE 17

2-trans-[2-(2-methyl-phenyl)-ethenyl]-3-propyl-4-oxo-4H-pyrido[1,2-a]pyrimidine-7-carboxylic acid (3.6 g) was reacted with 1-chloro-2-(diethylamino)ethane (2.7 g) and anhydrous K$_2$CO$_3$ (2.8 g) in dimethylformamide (40 ml) under stirring at 50° C. for 8 hours. After dilution with water, the precipitate was filtered off and washed with water until neutral: crystallization from isopropyl ether gave 2.1 g of 2-trans-[2-(2-methyl-phenyl)-ethenyl]-3-propyl-4-oxo-4H-pyrido[1,2-a]pyrimidine-7-carboxylic acid, 2-diethylamino-ethyl ester. By proceeding analogously, the following compounds were prepared:

2-trans-[2-(2-methyl-phenyl)-ethenyl]-3-propyl-6,7-methylen-4-oxo-4H-pyrido[1,2-a]pyrimidine-7-carboxylic acid, 2-(diethylamino)-ethyl ester;

2-trans-[2-(2-methyl-phenyl)-ethenyl]-3-ethyl-6,7-methylen-4-oxo-4H-pyrido[1,2-a]pyrimidine-7-carboxylic acid, 2-(diethylamino)-ethyl ester;

2-trans-[2-(3-methoxy-phenyl)-ethenyl]-3-ethyl-6,7-methylen-4-oxo-4H-pyrido[1,2-a]pyrimidine-7-carboxylic acid, 2-(diethylamino)-ethyl ester.

EXAMPLE 18

2-trans-[2-(2,3-dimethoxy-phenyl)-ethenyl]-3-ethyl-4-oxo-4H-pyrido[1,2-a]pyrimidine-7-carboxylic acid (1.2 g) was reacted with thionyl chloride (0.6 ml) in dioxane (20 ml) at reflux temperature for 3 hours, then the mixture was evaporated to dryness in vacuo. The residue was dissolved in dioxane (60 ml) and reacted with 2-(diethylamino)-ethanol (1.2 g) at room temperature for 20 hours. After dilution with water the precipitate was filtered off, dissolved in acetone (100 ml) and treated with the stoichiometric amount of HCl in ether: the precipitate was filtered off, washed with ethyl ether and dissolved in water. Alkalinization with $K_2CO_3$, filtration and crystallization from acetone gave 0.6 g of 2-trans-[2-(2,3-dimethoxy-phenyl)-ethenyl]-3-ethyl-4-oxo-4H-pyrido[1,2-a]pyrimidine-7-carboxylic acid, 2-(diethylamino) ethyl ester, m.p. 148°–150° C. By proceeding analogously the following compounds were prepared:

2-trans-[2-(2-methyl-phenyl)-ethenyl]-3-propyl-4-oxo-4H-pyrido[1,2-a]pyrimidine-7-carboxylic acid, 2-(diethylamino) ethyl ester;

2-trans-(2-phenyl-ethenyl)-3-methyl-4-oxo-4H-pyrido[1,2-a]pyrimidine-7-carboxylic acid, 2-(diethylamino) ethyl ester.

EXAMPLE 19

Trimethyl-sulphoxonium iodide (2.3 g) was reacted with 50% sodium hydride (0.5 g) in dimethylformamide (30 ml) under stirring at room temperature for 1 hour, then a solution of 2-trans-[2-(2,3-dimethoxy-phenyl)-ethenyl]-3-ethyl-4-oxo-4H-pyrido[1,2-a]pyrimidine-7-carboxylic acid, 2-(diethylamino)-ethyl ester (3.5 g) in dimethylformamide (20 ml) was added. The mixture was allowed to react under stirring at room temperature for 90 minutes, then it was diluted with water and extracted with ethyl acetate: organic layer was washed with water and evaporated to dryness in vacuo. The residue (2.9 g) was purified over a $SiO_2$ column using acetone as eluent: 1.9 g of 2-trans-[2-(2,3-dimethoxy-phenyl)-ethenyl]-3-ethyl-6,7-methylen-4-oxo-4H-pyrido[1,2-a]pyrimidine-7-carboxylic acid, 2-(diethylamino) ethyl ester, oil, were obtained, NMR (DMSO-d6) δ: 0.97 (t)

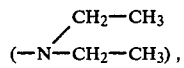

0.95–1.30 (m) (6,7-methylen proton and $-CH_2-\underline{CH_3}$), 2.54 (q)

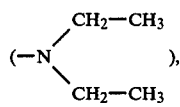

2.70 (t) ($-O-CH_2-\underline{CH_2}-N<$), 2.4–2.8 (m) (6,7-methylen proton and $\underline{CH_2}-CH_3$), 3.81 (s) ($-OCH_3$), 3.88 (s) ($-OCH_3$), 4.22 (t) ($-O-\underline{CH_2}-CH_2-N<$), 4.78 (d.d) (C-6 proton), 6.38 (d) (c-g proton), 7.18 (d) (C-8 proton), 7.39 (d) (H$_\beta$-vinyl proton), 8.07 (H$_\alpha$-vinyl proton), 7.18–7.46 (m) (phenyl protons).

EXAMPLE 20

By proceeding according to Examples 17, 18 and 19 the 2-dimethylaminoethyl-esters and the 2-(N-pyrrolidinyl)-ethyl-esters of the following compounds were prepared:

2-trans-[2-(2-methyl-phenyl)-ethenyl]-3-propyl-6,7-methylen-4-oxo-4H-pyrido[1,2-a]pyrimidine-7-carboxylic acid;

2-trans-(2-phenyl-ethenyl)-3-methyl-4-oxo-4H-pyrido[1,2-a]pyrimidine-7-carboxylic acid;

2-trans-[2-(3-methoxy-phenyl)-ethenyl]-3-ethyl-6,7-methylen-4-oxo-4H-pyrido[1,2-a]pyrimidine-7-carboxylic acid;

2-trans-[2-(2-methyl-phenyl)-ethenyl]-3-propyl-4-oxo-4H-pyrido[1,2-a]pyrimidine-7-carboxylic acid;

2-trans-(2-phenyl-ethenyl)-3-ethyl-6,7-methylen-4-oxo-4H-pyrido[1,2-a]pyrimidine-7-carboxylic acid;

2-trans-[2-(2-methyl-phenyl)-ethenyl]-3-ethyl-6,7-methylen-4-oxo-4H-pyrido[1,2-a]pyrimidine-7-carboxylic acid;

2-trans-[2-(2,3-dimethoxy-phenyl)-ethenyl]-3-ethyl-4-oxo-4H-pyrido[1,2-a]pyrimidine-7-carboxylic acid.

EXAMPLE 21

2-trans-[2-(2-methyl-phenyl)-ethenyl]-3-propyl-4-oxo-4H-pyrido[1,2-a]pyrimidine-7-carboxylic acid (5 g) was reacted with $NaHCO_3$ (1.25 g) in water (15 ml) at 80° C. until the solution was completed. After cooling to 5° C. a precipitate was obtained, which was filtered and washed with ice water. 2-trans-[2-(2-methyl-phenyl)-ethenyl]-3-propyl-4-oxo-4H-pyrido[1,2-a]pyrimidine-7-carboxylic acid, sodium salt (3.9 g) was obtained, m.p. >300° C. By proceeding analogously the following compounds were obtained:

2-trans-(2-phenyl-ethenyl)-3-methyl-4-oxo-4H-pyrido[1,2-a]pyrimidine-7-carboxylic acid, sodium salt, m.p. >300° C.;

2-trans-[2-(3-methoxy-phenyl)-ethenyl]-3-ethyl-6,7-methylen-4-oxo-4H-pyrido[1,2-a]pyrimidine-7-carboxylic acid, sodium salt, m.p. >300° C. (dec.).

EXAMPLE 22

Trimethyl-sulphoxonium iodide (3.39 g) was reacted with 50% sodium hydride (0.74 g) in dimethylformamide (70 ml) under stirring at room temperature for 60 minutes, then a solution of 2,3-dimethyl-4-oxo-4H-pyrido[1,2-a]pyrimidine-7-carboxylic acid, methyl ester, m.p. 130°–132° C. (3 g) in dimethylformamide (30 ml) was added. The mixture was allowed to react under stirring at room temperature for 1 hour, then it was diluted with ice water and extracted with ethyl acetate. After evaporation to dryness, the residue was crystallized from isopropyl ether to give 1.8 g of 2,3-dimethyl-6,7-methylen-4-oxo-4H-pyrido 1,2-a pyrimidine-7-carboxylic acid, methyl ester, m.p. 114°–116° C., which was reacted with 3-chlorobenzaldehyde (2.05 g) in methanol (70 ml) in the presence of sodium methoxide (1.1 g) under stirring at 60° C. for 24 hours. After cooling the reaction mixture was diluted in ice water, acidified with $NaH_2PO_4$ and extracted with ethyl acetate: after evaporation in vacuo of the solvent, the residue was purified over SiO$_2$ column using benzene-ethylacetate-acetic acid/40:10:0.5 as eluent. After purification with isopropyl ether 0.32 g of 2-trans-[2-(3-chorophenyl)-ethenyl]-3-methyl-6,7-methylen-4-oxo-4H-pyrido[1,2-a]pyrimidine-7-carboxylic acid, m.p. 190°-195° C. (dec), IR (C=O) acid 1710 cm$^{-1}$, (C=O) ketone 1665 cm$^{-1}$.

EXAMPLE 23

Tablets, each weighing 150 mg and containing 50 mg of the active substance are manufactured as follows:

| Compositions (for 10,000 tablets) | |
|---|---|
| 2-trans-[2-(3-methoxy-phenyl)-ethenyl]-3-ethyl-6,7-methylen-4-oxo-4H-pyrido[1,2-a]pyrimidine-7-carboxylic acid | 500 g |
| lactose | 710 g |
| corn starch | 237,5 g |
| talc powder | 37,5 g |
| magnesium stearate | 15 g |

2-trans-[2-(3-methoxy-phenyl)-ethenyl]-3-ethyl-6,7-methylen-4-oxo-4H-pyrido[1,2-a]pyrimidine-7-carboxylic acid, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of sieve size 1.4 mm, then the remaining quantity of starch, talc and magnesium stearate is added, carefully mixed, and processed into tablets using punches of 8 mm diameter.

EXAMPLE 24

| Aerosol formulation: | |
|---|---|
| 2-trans-[2-(3-methoxy-phenyl)-ethenyl]-3-ethyl-6,7-methylen-4-oxo-4H-pyrido[1,2-a]pyrimidine-7-carboxylic acid | 2% |
| ethanol | 10% |
| lecithin | 0.2% |
| mixture of dichlorofluoromethane and dichlorotetrafluoromethane (70:30 mixture) | ad 100%. |

What we claim is:
1. Compounds having the following general formula

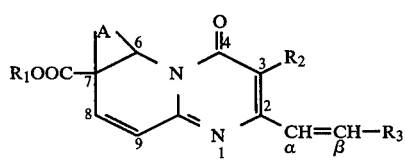

wherein A completes a bond, thereby providing a double bond between the 6- and 7-carbon atoms:

R$_1$ represents a hydrogen atom or a C$_1$-C$_{12}$ alkyl group which is unsubstituted or substituted by a

group, wherein each of R$_4$ and R$_5$ independently represents a hydrogen atom or a C$_1$-C$_{10}$ alkyl group, or R$_4$ and R$_5$, taken together with the nitrogen atom to which they are attached, form a N-pyrrolidinyl, piperidino or morpholino group;

R$_2$ represents a hydrogen atom or a C$_1$-C$_6$ alkyl group or a C$_3$- or C$_4$-alkenyl group;

R$_3$ represents (a) a furyl, thienyl or pyridyl group each of which is unsubstituted or substituted by a methyl group; or (b) a group of formula

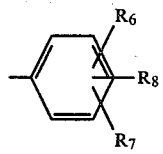

wherein each of R$_6$, R$_7$ and R$_8$ independently represents a hydrogen or halogen atom, a hydroxy group, a C$_1$-C$_4$ dialkylamino group, a group —CF$_3$ or a group —R$_9$ or —OR$_9$, where R$_9$ represents a C$_1$-C$_6$ alkyl or C$_3$- or C$_4$-alkenyl group and pharmaceutically acceptable salts thereof.

2. A compound having general formula (I) as for claim 1 wherein R$_{1a}$ is (a") hydrogen; (b") C$_1$-C$_6$ alkyl unsubstituted or substituted by a

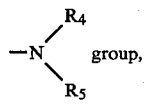

wherein each of R$_4$ and R$_5$, which are the same or different, is C$_1$-C$_4$ alkyl; (c") 2-(N-pyrrolidinyl)-ethyl; R$_2$ is C$_1$-C$_4$ alkyl; R$_3$ is (a''') phenyl unsubstituted or substituted by one to three chlorine, C$_1$-C$_4$ alkyl, or C$_1$-C$_4$ alkoxy substituents; or (b''') 2-furyl, 2-thienyl, 2-pyridyl, the furyl, the thienyl and the pyridyl groups being unsubstituted or substituted by a methyl group, as well as their pharmaceutically acceptable salts.

3. 2-trans-(2-phenyl-ethenyl)-3-propyl-4-oxo-4H-pyrido[1,2-a]-pyrimidine-7-carboxylic acid and its pharmaceutically acceptable salts, as claimed in claim 1.

4. 2-trans-[2-(2-methyl-phenyl)-ethenyl]-3-propyl-4-oxo-4H-pyrido-[1,2-a]pyrimidine-7-carboxylic acid and its pharmaceutically acceptable salts, as claimed in claim 1.

5. 2-trans-[2-(3-chloro-phenyl)-ethenyl]-3-methyl-4-oxo-4H-pyrido-[1,2-a]pyrimidine-7-carboxylic acid and its pharmaceutically acceptable salts, as claimed in claim 1.

6. 2-trans-[2-(4-methyl-phenyl)-ethenyl]-3-propyl-4-oxo-4H-pyrido-[1,2-a]pyrimidine-7-carboxylic acid and its pharmaceutically acceptable salts, as claimed in claim 1.

7. 2-trans-[2-(3-methoxy-phenyl)-ethenyl]-3-propyl-4-oxo-4H-pyrido[1,2-a]pyrimidine-7-carboxylic acid and its pharmaceutically acceptable salts, as claimed in claim 1.

8. 2-trans-[2-(2-ethoxy-phenyl)-ethenyl]-3-propyl-4-oxo-4H-pyrido-[1,2-a]pyrimidine-7-carboxylic acid and its pharmaceutically acceptable salts, as claimed in claim 1.

9. 2-trans-[2-(2,3-dimethoxy-phenyl)-ethenyl]-3-propyl-4-oxo-4H-pyrido[1,2-a]pyrimidine-7-carboxylic acid and its pharmaceutically acceptable salts, as claimed in claim 1.

10. 2-trans-[2-(2-thienyl)-ethenyl]-3-methyl-4-oxo-4H-pyrido[1,2-a]pyrimidine-7-carboxylic acid and its pharmaceutically acceptable salts, as claimed in claim 1.

11. 2-trans-[2-(2-furyl)-ethenyl]-3-methyl-4-oxo-4H-pyrido[1,2-a]pyrimidine-7-carboxylic acid and its pharmaceutically acceptable salts, as claimed in claim 1.

12. 2-trans-(2-phenyl-ethenyl)-3-methyl-4-oxo-4H-pyrido[1,2-a]pyrimidine-7-carboxylic acid and its pharmaceutically acceptable salts, as claimed in claim 1.

13. 2-trans-[2-(2-methoxy-3-ethoxy-phenyl)-ethenyl]-3-ethyl-4-oxo-4H-pyrido[1,2-a]pyrimidine-7-carboxylic acid and its pharmaceutically acceptable salts, as claimed in claim 1.

14. 2-trans-[2-(2-methoxy-phenyl)-ethenyl]-3-ethyl-4-oxo-4H-pyrido[1,2-a]pyrimidine-7-carboxylic acid and its pharmaceutically acceptable salts, as claimed in claim 1.

15. 2-trans-[2-(3-methoxy-phenyl)-ethenyl]-3-ethyl-4-oxo-4H-pyrido[1,2-a]pyrimidine-7-carboxylic acid and its pharmaceutically acceptable salts, as claimed in claim 1.

16. 2-trans-[2-(4-methoxy-phenyl)-ethenyl]-3-ethyl-4-oxo-4H-pyrido[1,2-a]pyrimidine-7-carboxylic acid and its pharmaceutically acceptable salts, as claimed in claim 1.

17. 2trans-[2-(2,3-dimethoxy-phenyl)-ethenyl]-3-ethyl-4-oxo-4H-pyrido[1,2-a]pyrimidine-7-carboxylic acid and its pharmaceutically acceptable salts, as claimed in claim 1.

18. 2-trans-[2-(3-chloro-phenyl)-ethenyl]-4-oxo-4H-pyrido[1,2-a]pyrimidine-7-carboxylic acid and its pharmaceutically acceptable salts, as claimed in claim 1.

19. 2-trans-[2-(2-methoxy-3-ethoxy-phenyl)-ethenyl]-3-propyl-4-oxo-4H-pyrido[1,2-a]pyrimidine-7-carboxylic acid and its pharmaceutically acceptable salts, as claimed in claim 1.

20. A compound as claimed in claim 2 wherein $R_2$ is $C_2$–$C_4$-alkyl.

21. A compound as claimed in claim 2 wherein $R_1$ is hydrogen and $R_2$ is $C_2$–$C_4$-alkyl.

22. A compound as claimed in claim 2 wherein $R_1$ is hydrogen, $R_2$ is $C_2$–$C_4$-alkyl and $R_3$ is ($a^{iv}$) phenyl unsubstituted or substituted by a $C_1$–$C_4$ alkyl or by one or two $C_1$–$C_4$ alkoxy groups, or ($b^{iv}$) 2-thienyl or 2-pyridyl; and the pharmaceutically or veterinarily acceptable salts thereof.

23. A compound as claimed in claim 2 wherein $R_3$ is phenyl substituted by a substituent selected from the group consisting of methyl, ethyl, methoxy, ethoxy, and isopropoxy.

24. A pharmaceutical composition suitable for use as an anti-allergy agent, said composition comprising a therapeutically effective amount of a compound as claimed in any one of claims 1, 2, 23, 20, 21 or 22 in association with a pharmaceutical acceptable carrier or diluent.

25. A pharmaceutical composition suitable for use as an anti-ulcer agent, said composition comprising a therapeutically effective amount of a compound as claimed in any one of claims 1, 2, 23, 20, 21 or 22 in association with a pharmaceutically acceptable carrier or diluent.

26. A pharmaceutical composition suitable for use as an anti-diabetic agent, said composition comprising a therapeutically effective amount of a compound as claimed in any one of claims 1, 2, 23, 20, 21 or 22 in association with a pharmaceutically acceptable carrier or diluent.

27. A method of producing an anti-allergy effect in a patient in need of such effect, said method comprising administering to said patient an anti-allergy effective amount of a compound as claimed in any one of claims 3–19, 1, 2, 20, 21 or 22.

28. A method of producing an anti-ulcer effect in a patient in need of such effect, said method comprising administering to said patient an anti-ulcer effective amount of a compound as claimed in any one of claims 3–19, 1, 2, 23, 20, 21 or 22.

29. A method of producing an anti-diabetic effect in a patient in need of such effect, said method comprising administering to said patient an anti-diabetic effective amount of a compound as claimed in any one of claims 3–19, 1, 2, 20, 21 or 22.

* * * * *

UNITED STATES PATENT AND TRADEMARK OFFICE
CERTIFICATE OF CORRECTION

PATENT NO. : 4,341,780
DATED : July 27, 1982
INVENTOR(S) : GIANFEDERICO DORIA et al It is certified that error appears in the above—identified patent and that said Letters Patent is hereby corrected as shown below:

Item [63] "Continuation" should be --Division--.

Column 30, line 24, "$R_{1u}$" should be --$R_1$--.

Column 32, lines 31 and 41, after "2" insert --23--.

*Signed and Sealed this*

*Eighth* Day of *November 1983*

[SEAL]

*Attest:*

GERALD J. MOSSINGHOFF

*Attesting Officer*     *Commissioner of Patents and Trademarks*